US010494406B2

(12) United States Patent
Sawada et al.

(10) Patent No.: US 10,494,406 B2
(45) Date of Patent: Dec. 3, 2019

(54) VACCINE ANTIGEN WITH INCREASED IMMUNOGENICITY

(71) Applicant: IDEMITSU KOSAN CO., LTD., Chiyoda-ku (JP)

(72) Inventors: Kazutoshi Sawada, Sodegaura (JP); Takeshi Matsui, Sodegaura (JP)

(73) Assignee: IDEMITSU KOSAN CO., LTD., Chiyoda-ku (JP)

(*) Notice: Subject to any disclaimer, the term of this patent is extended or adjusted under 35 U.S.C. 154(b) by 0 days.

(21) Appl. No.: 15/779,106

(22) PCT Filed: Nov. 30, 2016

(86) PCT No.: PCT/JP2016/085606

§ 371 (c)(1),
(2) Date: May 25, 2018

(87) PCT Pub. No.: WO2017/094793

PCT Pub. Date: Jun. 8, 2017

(65) Prior Publication Data

US 2018/0265553 A1 Sep. 20, 2018

(30) Foreign Application Priority Data

Nov. 30, 2015 (JP) ................................ 2015-233714
Feb. 9, 2016 (JP) ................................ 2016-023090

(51) Int. Cl.

| | |
|---|---|
| ***C07K 14/005*** | (2006.01) |
| ***C12N 7/00*** | (2006.01) |
| ***C07K 14/25*** | (2006.01) |
| ***C07K 14/245*** | (2006.01) |
| ***C07K 14/28*** | (2006.01) |
| ***A01H 5/00*** | (2018.01) |
| ***A61K 39/00*** | (2006.01) |
| ***A61K 36/28*** | (2006.01) |
| ***C07K 19/00*** | (2006.01) |
| ***C07K 14/405*** | (2006.01) |
| ***C12N 15/09*** | (2006.01) |
| ***A23K 20/195*** | (2016.01) |

(52) U.S. Cl.

CPC ............. *C07K 14/005* (2013.01); *A01H 5/00* (2013.01); *A23K 20/195* (2016.05); *A61K 36/28* (2013.01); *A61K 39/00* (2013.01); *C07K 14/245* (2013.01); *C07K 14/25* (2013.01); *C07K 14/28* (2013.01); *C07K 14/405* (2013.01); *C07K 19/00* (2013.01); *C12N 7/00* (2013.01); *C12N 15/09* (2013.01); *C07K 2319/55* (2013.01); *C12N 2750/14322* (2013.01); *Y02A 50/472* (2018.01)

(58) Field of Classification Search

None

See application file for complete search history.

(56) References Cited

U.S. PATENT DOCUMENTS

| | | | |
|---|---|---|---|
| 2004/0146534 A1 | 7/2004 | Glenn et al. |
| 2011/0231960 A1 | 9/2011 | Sawada et al. |
| 2013/0156802 A1 | 6/2013 | Tinker |
| 2015/0133635 A1 | 5/2015 | Sawada et al. |
| 2017/0028046 A1 | 2/2017 | Sawada et al. |

FOREIGN PATENT DOCUMENTS

| | | | |
|---|---|---|---|
| EP | 3 18 930 | | 6/1989 |
| EP | 2 287 300 | * | 2/2011 |
| JP | 2005-504002 A | | 2/2005 |
| JP | 2012-19719 A | | 2/2012 |
| JP | 5360727 B2 | | 12/2013 |
| WO | WO 96/34893 | | 11/1996 |
| WO | WO 2006/011151 | | 2/2006 |
| WO | WO 2015/080100 A1 | | 6/2015 |

OTHER PUBLICATIONS

Sequence alignment of instant Seq ID No. 16 with Geneseq database access No. AAY29607 by Snow et al. 1999.*
Wu et al. (Virology. 2003; 313: 337-342).*
Alignment of Seq ID No. 33 with 2004 Geneseq database access No. ADP21006 by Palmer et al. in WO2004032622.*
Mercenier et al. (Current Opinion in Biotechnology. 2001; 12 (5): 510-515).*
International Search Report dated Feb. 28, 2017 in PCT/JP2016/085606 filed Nov. 30, 2016.
Klipstein, F. A. et al., "Mucosal Antitoxin Response in Volunteers to Immunization with a Synthetic Peptide of *Escherichia coli* Heat-Stable Enterotoxin", Infection and Immunity, Oct. 1985, vol. 50, No. 1, pp. 328-332.
Clements, J. D., "Construction of a Nontoxic Fusion Peptide for Immunization against *Escherichia coli* Strains That Produce Heat-Labile and Heat-Stable Enterotoxins", Infection and Immunity, May 1990, vol. 58, No. 5, pp. 1159-1166.
Zhang, W. et al., "Genetic Fusions of Heat-Labile Toxoid (LT) and Heat-Stable Toxin b (STb) of Porcine Enterotoxigenic *Escherichia coli* Elicit Protective Anti-LT and Anti-STb Antibodies", Clinical and Vaccine Immunology, Aug. 2010, vol. 17, No. 8, pp. 1223-1231.
Rosales-Mendoza, S. et al., "Immunogenicity of nuclear-encoded LTB:ST fusion protein from *Escherichia coli* expressed in tobacco plants", Plant Cell Reports, Feb. 12, 2011, vol. 30, pp. 1145-1152.

(Continued)

*Primary Examiner* — Shanon A. Foley
(74) *Attorney, Agent, or Firm* — Oblon, McClelland, Maier & Neustadt, L.L.P.

(57) ABSTRACT

According to the invention, immunogenicity of an antigenic peptide is increased by administering a fusion protein, which comprises an antigenic peptide and an adjuvant protein, wherein the adjuvant protein comprises two or more proteins selected from the group consisting of a Shiga toxin 2e B subunit (Stx2eB), an *Escherichia coli* heat-labile toxin B subunit (LTB), and a cholera toxin B subunit (CTB). or a transformant transformed by a gene coding for the fusion protein.

20 Claims, 7 Drawing Sheets

Specification includes a Sequence Listing.

(56) References Cited

OTHER PUBLICATIONS

X. Ran, et al., "The immunogenicity of fusion protein linking the carboxyl terminus of the B subunit of Shiga toxin 2 to the B subunit of *E. coli* heat-labile enterotoxin", Veterinary Microbiology, vol. 127, 2008, pp. 209-215.
European Search Report issued in corresponding European Application No. 16870730.5 dated Mar. 29, 2019.

* cited by examiner

Plant expression plasmid

[Plasmid map: LB – NOS T – NPT II – NOS pro. – 35S pro. – NtADH mod – SP – [insert] – HSP T – RB]

LTB—mSTp

LTB—Stx2eB—mSTp

Stx2eB—LTB—mSTp mice → 1w ↓ 1w ↓ 1w ↓ 1w ↓ 1w ↑ small intestine wash fluid

1. Empty vector (negative control)
2. Porcine rotavirus type C
3. Porcine epidemic diarrhea virus
4. Porcine parvovirus
5. Canine parvovirus
6. Feline immunodeficiency virus

SEQUENCE LISTING

```
<160> NUMBER OF SEQ ID NOS: 68

<210> SEQ ID NO 1
<211> LENGTH: 36
<212> TYPE: DNA
<213> ORGANISM: Artificial Sequence
<220> FEATURE:
<223> OTHER INFORMATION: an artificially synthesized DNA

<400> SEQUENCE: 1
```

agatcccctg gttctggtcc tggttctcct agatcc 36

<210> SEQ ID NO 2
<211> LENGTH: 12
<212> TYPE: PRT
<213> ORGANISM: Artificial Sequence
<220> FEATURE:
<223> OTHER INFORMATION: an artificially synthesized peptide

<400> SEQUENCE: 2

Arg Ser Pro Gly Ser Gly Pro Gly Ser Pro Arg Ser
1 5 10

<210> SEQ ID NO 3
<211> LENGTH: 36
<212> TYPE: DNA
<213> ORGANISM: Artificial Sequence
<220> FEATURE:
<223> OTHER INFORMATION: an artificially synthesized DNA

<400> SEQUENCE: 3
agaggacctg gttctggtcc tggttctcct agatct 36

<210> SEQ ID NO 4
<211> LENGTH: 12
<212> TYPE: PRT
<213> ORGANISM: Artificial Sequence
<220> FEATURE:
<223> OTHER INFORMATION: an artificially synthesized peptide

<400> SEQUENCE: 4

Arg Gly Pro Gly Ser Gly Pro Gly Ser Pro Arg Ser
1 5 10

<210> SEQ ID NO 5
<211> LENGTH: 312
<212> TYPE: DNA
<213> ORGANISM: Vibrio cholerae

<400> SEQUENCE: 5
accccccaga acatcaccga cctctgcgcc gagagccaca acacccaaat ctacaccctc 60
aacgacaaga ttttcagcta caccgagagc ctcgccggca agagggagat ggccatcatc 120
accttcaaga acggcgccat cttccaggtc gaggtccccg gcagccagca catcgacagc 180
cagaagaagg ccatcgagag gatgaaggac accctcagga tcgcctacct caccgaggcc 240
aaggtcgaga agctctgcgt ctggaacaac aagacccccc acgccatcgc cgccatcagc 300
atggccaact ga 312

<210> SEQ ID NO 6
<211> LENGTH: 103
<212> TYPE: PRT
<213> ORGANISM: Vibrio cholerae

<400> SEQUENCE: 6

Thr Pro Gln Asn Ile Thr Asp Leu Cys Ala Glu Ser His Asn Thr Gln
1 5 10 15

Ile Tyr Thr Leu Asn Asp Lys Ile Phe Ser Tyr Thr Glu Ser Leu Ala
20 25 30

Gly Lys Arg Glu Met Ala Ile Ile Thr Phe Lys Asn Gly Ala Ile Phe
35 40 45

Gln Val Glu Val Pro Gly Ser Gln His Ile Asp Ser Gln Lys Lys Ala

```
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn
            100


<210> SEQ ID NO 7
<211> LENGTH: 210
<212> TYPE: DNA
<213> ORGANISM: Escherichia coli

<400> SEQUENCE: 7

gcggcggact gcgcgaaggg caagatcgag ttctcgaagt acaacgagga caacacgttc      60

acggtcaagg tctcgggccg cgagtactgg acgaaccgct ggaacctgca gccgctgctg     120

cagtcggcgc agctgacggg catgacggtc acgatcatct cgaacacgtg ctcgtcgggc     180

tcgggcttcg cgcaggtcaa gttcaactga                                      210


<210> SEQ ID NO 8
<211> LENGTH: 69
<212> TYPE: PRT
<213> ORGANISM: Escherichia coli

<400> SEQUENCE: 8

Ala Ala Asp Cys Ala Lys Gly Lys Ile Glu Phe Ser Lys Tyr Asn Glu
1               5                   10                  15

Asp Asn Thr Phe Thr Val Lys Val Ser Gly Arg Glu Tyr Trp Thr Asn
            20                  25                  30

Arg Trp Asn Leu Gln Pro Leu Leu Gln Ser Ala Gln Leu Thr Gly Met
        35                  40                  45

Thr Val Thr Ile Ile Ser Asn Thr Cys Ser Ser Gly Ser Gly Phe Ala
    50                  55                  60

Gln Val Lys Phe Asn
65


<210> SEQ ID NO 9
<211> LENGTH: 210
<212> TYPE: DNA
<213> ORGANISM: Artificial Sequence
<220> FEATURE:
<223> OTHER INFORMATION: artificially synthesized polynucleotide

<400> SEQUENCE: 9

gcggcggact gcgcgaaggg caagatcgag ttctcgaagt acaacgagga caacacgttc      60

acggtcaagg tctcgggccg cgagtactgg acgaaccgct ggaacctgca gccgctgctg     120

cagtcggcgc agctgacggg catgacggtc acgatcatct cgtcgacgtg ctcgtcgggc     180

tcgggcttcg cgcaggtcaa gttcaactga                                      210


<210> SEQ ID NO 10
<211> LENGTH: 69
<212> TYPE: PRT
<213> ORGANISM: Artificial Sequence
<220> FEATURE:
<223> OTHER INFORMATION: an artificially synthesized polypeptide

<400> SEQUENCE: 10

Ala Ala Asp Cys Ala Lys Gly Lys Ile Glu Phe Ser Lys Tyr Asn Glu
```

-continued

```
1               5                   10                  15

Asp Asn Thr Phe Thr Val Lys Val Ser Gly Arg Glu Tyr Trp Thr Asn
            20                  25                  30

Arg Trp Asn Leu Gln Pro Leu Leu Gln Ser Ala Gln Leu Thr Gly Met
        35                  40                  45

Thr Val Thr Ile Ile Ser Ser Thr Cys Ser Ser Gly Ser Gly Phe Ala
    50                  55                  60

Gln Val Lys Phe Asn
65


<210> SEQ ID NO 11
<211> LENGTH: 309
<212> TYPE: DNA
<213> ORGANISM: Escherichia coli

<400> SEQUENCE: 11

gccccccaga ccatcaccga gttgtgcagc gagtaccgca acacccaaat ctacaccatc     60

aacgacaaga tcctcagcta caccgagagc atggccggca agagggagat ggtgatcatc    120

accttcaaga gcggcgagac cttccaggtc gaggtccccg gcagccagca catcgacagc    180

cagaagaagg ccatcgagag gatgaaggac accctcagga tcacctacct caccgagacc    240

aagatcgaca agctctgcgt ctggaacaac aagacccca acagcatcgc cgccatcagc    300

atggagaac                                                            309


<210> SEQ ID NO 12
<211> LENGTH: 103
<212> TYPE: PRT
<213> ORGANISM: Escherichia coli

<400> SEQUENCE: 12

Ala Pro Gln Thr Ile Thr Glu Leu Cys Ser Glu Tyr Arg Asn Thr Gln
1               5                   10                  15

Ile Tyr Thr Ile Asn Asp Lys Ile Leu Ser Tyr Thr Glu Ser Met Ala
            20                  25                  30

Gly Lys Arg Glu Met Val Ile Ile Thr Phe Lys Ser Gly Glu Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Thr Tyr Leu Thr Glu Thr
65                  70                  75                  80

Lys Ile Asp Lys Leu Cys Val Trp Asn Asn Lys Thr Pro Asn Ser Ile
                85                  90                  95

Ala Ala Ile Ser Met Glu Asn
            100


<210> SEQ ID NO 13
<211> LENGTH: 309
<212> TYPE: DNA
<213> ORGANISM: Artificial Sequence
<220> FEATURE:
<223> OTHER INFORMATION: an artificially synthesized polynucleotide

<400> SEQUENCE: 13

gccccccaga ccatcaccga gttgtgcagc gagtaccgca acacccaaat ctacaccatc     60

aacgacaaga tcctcagcta caccgagagc atggccggca agagggagat ggtgatcatc    120

accttcaaga gcggcgagac cttccaggtc gaggtccccg gcagccagca catcgacagc    180
```

-continued

```
cagaagaagg ccatcgagag gatgaaggac accctcagga tcacctacct caccgagacc    240

aagatcgaca agctctgcgt ctggaacagc aagaccccca acagcatcgc cgccatcagc    300

atggagaac                                                            309


<210> SEQ ID NO 14
<211> LENGTH: 103
<212> TYPE: PRT
<213> ORGANISM: Artificial Sequence
<220> FEATURE:
<223> OTHER INFORMATION: an artificially synthesized polypeptide

<400> SEQUENCE: 14

Ala Pro Gln Thr Ile Thr Glu Leu Cys Ser Glu Tyr Arg Asn Thr Gln
1               5                   10                  15

Ile Tyr Thr Ile Asn Asp Lys Ile Leu Ser Tyr Thr Glu Ser Met Ala
            20                  25                  30

Gly Lys Arg Glu Met Val Ile Ile Thr Phe Lys Ser Gly Glu Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Thr Tyr Leu Thr Glu Thr
65                  70                  75                  80

Lys Ile Asp Lys Leu Cys Val Trp Asn Ser Lys Thr Pro Asn Ser Ile
                85                  90                  95

Ala Ala Ile Ser Met Glu Asn
            100


<210> SEQ ID NO 15
<211> LENGTH: 54
<212> TYPE: DNA
<213> ORGANISM: Artificial Sequence
<220> FEATURE:
<223> OTHER INFORMATION: mSTp
<220> FEATURE:
<221> NAME/KEY: CDS
<222> LOCATION: (1)..(54)

<400> SEQUENCE: 15

aac acc ttc tac tgc tgc gag ttg tgc tgc aac ccc ttg tgc gcc ggc       48
Asn Thr Phe Tyr Cys Cys Glu Leu Cys Cys Asn Pro Leu Cys Ala Gly
1               5                   10                  15

tgc tac                                                               54
Cys Tyr


<210> SEQ ID NO 16
<211> LENGTH: 18
<212> TYPE: PRT
<213> ORGANISM: Artificial Sequence
<220> FEATURE:
<223> OTHER INFORMATION: Synthetic Construct

<400> SEQUENCE: 16

Asn Thr Phe Tyr Cys Cys Glu Leu Cys Cys Asn Pro Leu Cys Ala Gly
1               5                   10                  15

Cys Tyr


<210> SEQ ID NO 17
<211> LENGTH: 402
<212> TYPE: DNA
<213> ORGANISM: Artificial Sequence
<220> FEATURE:
<223> OTHER INFORMATION: LTB-mSTp
```

```
<220> FEATURE:
<221> NAME/KEY: CDS
<222> LOCATION: (1)..(399)

<400> SEQUENCE: 17

gcc ccc cag acc atc acc gag ttg tgc agc gag tac cgc aac acc caa       48
Ala Pro Gln Thr Ile Thr Glu Leu Cys Ser Glu Tyr Arg Asn Thr Gln
1               5                   10                  15

atc tac acc atc aac gac aag atc ctc agc tac acc gag agc atg gcc       96
Ile Tyr Thr Ile Asn Asp Lys Ile Leu Ser Tyr Thr Glu Ser Met Ala
            20                  25                  30

ggc aag agg gag atg gtg atc atc acc ttc aag agc ggc gag acc ttc      144
Gly Lys Arg Glu Met Val Ile Ile Thr Phe Lys Ser Gly Glu Thr Phe
        35                  40                  45

cag gtc gag gtc ccc ggc agc cag cac atc gac agc cag aag aag gcc      192
Gln Val Glu Val Pro Gly Ser Gln His Ile Asp Ser Gln Lys Lys Ala
    50                  55                  60

atc gag agg atg aag gac acc ctc agg atc acc tac ctc acc gag acc      240
Ile Glu Arg Met Lys Asp Thr Leu Arg Ile Thr Tyr Leu Thr Glu Thr
65                  70                  75                  80

aag atc gac aag ctc tgc gtc tgg aac aac aag acc ccc aac agc atc      288
Lys Ile Asp Lys Leu Cys Val Trp Asn Asn Lys Thr Pro Asn Ser Ile
                85                  90                  95

gcc gcc atc agc atg gag aac aga tcc cct ggt tct ggt cct ggt tct      336
Ala Ala Ile Ser Met Glu Asn Arg Ser Pro Gly Ser Gly Pro Gly Ser
            100                 105                 110

cct aga tcc aac acc ttc tac tgc tgc gag ttg tgc tgc aac ccc ttg      384
Pro Arg Ser Asn Thr Phe Tyr Cys Cys Glu Leu Cys Cys Asn Pro Leu
        115                 120                 125

tgc gcc ggc tgc tac tga                                              402
Cys Ala Gly Cys Tyr
    130


<210> SEQ ID NO 18
<211> LENGTH: 133
<212> TYPE: PRT
<213> ORGANISM: Artificial Sequence
<220> FEATURE:
<223> OTHER INFORMATION: Synthetic Construct

<400> SEQUENCE: 18

Ala Pro Gln Thr Ile Thr Glu Leu Cys Ser Glu Tyr Arg Asn Thr Gln
1               5                   10                  15

Ile Tyr Thr Ile Asn Asp Lys Ile Leu Ser Tyr Thr Glu Ser Met Ala
            20                  25                  30

Gly Lys Arg Glu Met Val Ile Ile Thr Phe Lys Ser Gly Glu Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Thr Tyr Leu Thr Glu Thr
65                  70                  75                  80

Lys Ile Asp Lys Leu Cys Val Trp Asn Asn Lys Thr Pro Asn Ser Ile
                85                  90                  95

Ala Ala Ile Ser Met Glu Asn Arg Ser Pro Gly Ser Gly Pro Gly Ser
            100                 105                 110

Pro Arg Ser Asn Thr Phe Tyr Cys Cys Glu Leu Cys Cys Asn Pro Leu
        115                 120                 125

Cys Ala Gly Cys Tyr
    130
```

```
<210> SEQ ID NO 19
<211> LENGTH: 645
<212> TYPE: DNA
<213> ORGANISM: Artificial Sequence
<220> FEATURE:
<223> OTHER INFORMATION: LTB-Stx2eB-mSTp
<220> FEATURE:
<221> NAME/KEY: CDS
<222> LOCATION: (1)..(642)

<400> SEQUENCE: 19

gcc ccc cag acc atc acc gag ttg tgc agc gag tac cgc aac acc caa       48
Ala Pro Gln Thr Ile Thr Glu Leu Cys Ser Glu Tyr Arg Asn Thr Gln
1               5                   10                  15

atc tac acc atc aac gac aag atc ctc agc tac acc gag agc atg gcc       96
Ile Tyr Thr Ile Asn Asp Lys Ile Leu Ser Tyr Thr Glu Ser Met Ala
            20                  25                  30

ggc aag agg gag atg gtg atc atc acc ttc aag agc ggc gag acc ttc      144
Gly Lys Arg Glu Met Val Ile Ile Thr Phe Lys Ser Gly Glu Thr Phe
        35                  40                  45

cag gtc gag gtc ccc ggc agc cag cac atc gac agc cag aag aag gcc      192
Gln Val Glu Val Pro Gly Ser Gln His Ile Asp Ser Gln Lys Lys Ala
    50                  55                  60

atc gag agg atg aag gac acc ctc agg atc acc tac ctc acc gag acc      240
Ile Glu Arg Met Lys Asp Thr Leu Arg Ile Thr Tyr Leu Thr Glu Thr
65                  70                  75                  80

aag atc gac aag ctc tgc gtc tgg aac aac aag acc ccc aac agc atc      288
Lys Ile Asp Lys Leu Cys Val Trp Asn Asn Lys Thr Pro Asn Ser Ile
                85                  90                  95

gcc gcc atc agc atg gag aac aga tcc cct ggt tct ggt cct ggt tct      336
Ala Ala Ile Ser Met Glu Asn Arg Ser Pro Gly Ser Gly Pro Gly Ser
            100                 105                 110

cct aga tcc gcg gcg gac tgc gcg aag ggc aag atc gag ttc tcg aag      384
Pro Arg Ser Ala Ala Asp Cys Ala Lys Gly Lys Ile Glu Phe Ser Lys
        115                 120                 125

tac aac gag gac aac acg ttc acg gtc aag gtc tcg ggc cgc gag tac      432
Tyr Asn Glu Asp Asn Thr Phe Thr Val Lys Val Ser Gly Arg Glu Tyr
    130                 135                 140

tgg acg aac cgc tgg aac ctg cag ccg ctg ctg cag tcg gcg cag ctg      480
Trp Thr Asn Arg Trp Asn Leu Gln Pro Leu Leu Gln Ser Ala Gln Leu
145                 150                 155                 160

acg ggc atg acg gtc acg atc atc tcg tcg acg tgc tcg tcg ggc tcg      528
Thr Gly Met Thr Val Thr Ile Ile Ser Ser Thr Cys Ser Ser Gly Ser
                165                 170                 175

ggc ttc gcg cag gtc aag ttc aac aga gga cct ggt tct ggt cct ggt      576
Gly Phe Ala Gln Val Lys Phe Asn Arg Gly Pro Gly Ser Gly Pro Gly
            180                 185                 190

tct cct aga tcc aac acc ttc tac tgc tgc gag ttg tgc tgc aac ccc      624
Ser Pro Arg Ser Asn Thr Phe Tyr Cys Cys Glu Leu Cys Cys Asn Pro
        195                 200                 205

ttg tgc gcc ggc tgc tac tga                                          645
Leu Cys Ala Gly Cys Tyr
    210


<210> SEQ ID NO 20
<211> LENGTH: 214
<212> TYPE: PRT
<213> ORGANISM: Artificial Sequence
<220> FEATURE:
<223> OTHER INFORMATION: Synthetic Construct

<400> SEQUENCE: 20
```

```
Ala Pro Gln Thr Ile Thr Glu Leu Cys Ser Glu Tyr Arg Asn Thr Gln
1               5                   10                  15

Ile Tyr Thr Ile Asn Asp Lys Ile Leu Ser Tyr Thr Glu Ser Met Ala
            20                  25                  30

Gly Lys Arg Glu Met Val Ile Ile Thr Phe Lys Ser Gly Glu Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Thr Tyr Leu Thr Glu Thr
65                  70                  75                  80

Lys Ile Asp Lys Leu Cys Val Trp Asn Asn Lys Thr Pro Asn Ser Ile
                85                  90                  95

Ala Ala Ile Ser Met Glu Asn Arg Ser Pro Gly Ser Gly Pro Gly Ser
            100                 105                 110

Pro Arg Ser Ala Ala Asp Cys Ala Lys Gly Lys Ile Glu Phe Ser Lys
        115                 120                 125

Tyr Asn Glu Asp Asn Thr Phe Thr Val Lys Val Ser Gly Arg Glu Tyr
    130                 135                 140

Trp Thr Asn Arg Trp Asn Leu Gln Pro Leu Leu Gln Ser Ala Gln Leu
145                 150                 155                 160

Thr Gly Met Thr Val Thr Ile Ile Ser Ser Thr Cys Ser Ser Gly Ser
                165                 170                 175

Gly Phe Ala Gln Val Lys Phe Asn Arg Gly Pro Gly Ser Gly Pro Gly
            180                 185                 190

Ser Pro Arg Ser Asn Thr Phe Tyr Cys Cys Glu Leu Cys Cys Asn Pro
        195                 200                 205

Leu Cys Ala Gly Cys Tyr
    210


<210> SEQ ID NO 21
<211> LENGTH: 645
<212> TYPE: DNA
<213> ORGANISM: Artificial Sequence
<220> FEATURE:
<223> OTHER INFORMATION: Stx2eB-LTB-mSTp
<220> FEATURE:
<221> NAME/KEY: CDS
<222> LOCATION: (1)..(642)

<400> SEQUENCE: 21

gcg gcg gac tgc gcg aag ggc aag atc gag ttc tcg aag tac aac gag       48
Ala Ala Asp Cys Ala Lys Gly Lys Ile Glu Phe Ser Lys Tyr Asn Glu
1               5                   10                  15

gac aac acg ttc acg gtc aag gtc tcg ggc cgc gag tac tgg acg aac       96
Asp Asn Thr Phe Thr Val Lys Val Ser Gly Arg Glu Tyr Trp Thr Asn
            20                  25                  30

cgc tgg aac ctg cag ccg ctg ctg cag tcg gcg cag ctg acg ggc atg      144
Arg Trp Asn Leu Gln Pro Leu Leu Gln Ser Ala Gln Leu Thr Gly Met
        35                  40                  45

acg gtc acg atc atc tcg tcg acg tgc tcg tcg ggc tcg ggc ttc gcg      192
Thr Val Thr Ile Ile Ser Ser Thr Cys Ser Ser Gly Ser Gly Phe Ala
    50                  55                  60

cag gtc aag ttc aac aga gga cct ggt tct ggt cct ggt tct cct aga      240
Gln Val Lys Phe Asn Arg Gly Pro Gly Ser Gly Pro Gly Ser Pro Arg
65                  70                  75                  80

tcc gcc ccc cag acc atc acc gag ttg tgc agc gag tac cgc aac acc      288
Ser Ala Pro Gln Thr Ile Thr Glu Leu Cys Ser Glu Tyr Arg Asn Thr
                85                  90                  95
```

-continued

```
caa atc tac acc atc aac gac aag atc ctc agc tac acc gag agc atg      336
Gln Ile Tyr Thr Ile Asn Asp Lys Ile Leu Ser Tyr Thr Glu Ser Met
            100                 105                 110

gcc ggc aag agg gag atg gtg atc atc acc ttc aag agc ggc gag acc      384
Ala Gly Lys Arg Glu Met Val Ile Ile Thr Phe Lys Ser Gly Glu Thr
        115                 120                 125

ttc cag gtc gag gtc ccc ggc agc cag cac atc gac agc cag aag aag      432
Phe Gln Val Glu Val Pro Gly Ser Gln His Ile Asp Ser Gln Lys Lys
    130                 135                 140

gcc atc gag agg atg aag gac acc ctc agg atc acc tac ctc acc gag      480
Ala Ile Glu Arg Met Lys Asp Thr Leu Arg Ile Thr Tyr Leu Thr Glu
145                 150                 155                 160

acc aag atc gac aag ctc tgc gtc tgg aac aac aag acc ccc aac agc      528
Thr Lys Ile Asp Lys Leu Cys Val Trp Asn Asn Lys Thr Pro Asn Ser
                165                 170                 175

atc gcc gcc atc agc atg gag aac aga tcc cct ggt tct ggt cct ggt      576
Ile Ala Ala Ile Ser Met Glu Asn Arg Ser Pro Gly Ser Gly Pro Gly
            180                 185                 190

tct cct aga tcc aac acc ttc tac tgc tgc gag ttg tgc tgc aac ccc      624
Ser Pro Arg Ser Asn Thr Phe Tyr Cys Cys Glu Leu Cys Cys Asn Pro
        195                 200                 205

ttg tgc gcc ggc tgc tac tga                                          645
Leu Cys Ala Gly Cys Tyr
    210


<210> SEQ ID NO 22
<211> LENGTH: 214
<212> TYPE: PRT
<213> ORGANISM: Artificial Sequence
<220> FEATURE:
<223> OTHER INFORMATION: Synthetic Construct

<400> SEQUENCE: 22

Ala Ala Asp Cys Ala Lys Gly Lys Ile Glu Phe Ser Lys Tyr Asn Glu
1               5                   10                  15

Asp Asn Thr Phe Thr Val Lys Val Ser Gly Arg Glu Tyr Trp Thr Asn
            20                  25                  30

Arg Trp Asn Leu Gln Pro Leu Leu Gln Ser Ala Gln Leu Thr Gly Met
        35                  40                  45

Thr Val Thr Ile Ile Ser Ser Thr Cys Ser Ser Gly Ser Gly Phe Ala
    50                  55                  60

Gln Val Lys Phe Asn Arg Gly Pro Gly Ser Gly Pro Gly Ser Pro Arg
65                  70                  75                  80

Ser Ala Pro Gln Thr Ile Thr Glu Leu Cys Ser Glu Tyr Arg Asn Thr
                85                  90                  95

Gln Ile Tyr Thr Ile Asn Asp Lys Ile Leu Ser Tyr Thr Glu Ser Met
            100                 105                 110

Ala Gly Lys Arg Glu Met Val Ile Ile Thr Phe Lys Ser Gly Glu Thr
        115                 120                 125

Phe Gln Val Glu Val Pro Gly Ser Gln His Ile Asp Ser Gln Lys Lys
    130                 135                 140

Ala Ile Glu Arg Met Lys Asp Thr Leu Arg Ile Thr Tyr Leu Thr Glu
145                 150                 155                 160

Thr Lys Ile Asp Lys Leu Cys Val Trp Asn Asn Lys Thr Pro Asn Ser
                165                 170                 175

Ile Ala Ala Ile Ser Met Glu Asn Arg Ser Pro Gly Ser Gly Pro Gly
            180                 185                 190

Ser Pro Arg Ser Asn Thr Phe Tyr Cys Cys Glu Leu Cys Cys Asn Pro
```

-continued

```
        195                 200                 205

Leu Cys Ala Gly Cys Tyr
    210


<210> SEQ ID NO 23
<211> LENGTH: 35
<212> TYPE: DNA
<213> ORGANISM: Artificial Sequence
<220> FEATURE:
<223> OTHER INFORMATION: primer

<400> SEQUENCE: 23

gatccaacac cttctactgc tgcgagttgt gctgc                                35


<210> SEQ ID NO 24
<211> LENGTH: 41
<212> TYPE: DNA
<213> ORGANISM: Artificial Sequence
<220> FEATURE:
<223> OTHER INFORMATION: primer

<400> SEQUENCE: 24

gatctgtagc agccggcgca caaggggttg cagcacaact c                         41


<210> SEQ ID NO 25
<211> LENGTH: 17
<212> TYPE: PRT
<213> ORGANISM: Artificial Sequence
<220> FEATURE:
<223> OTHER INFORMATION: an artificially synthesized peptide

<400> SEQUENCE: 25

Arg Ser Pro Gly Ser Gly Pro Gly Ser Pro Arg Ser Pro Gly Ser Arg
1               5                   10                  15

Ser


<210> SEQ ID NO 26
<211> LENGTH: 22
<212> TYPE: PRT
<213> ORGANISM: Artificial Sequence
<220> FEATURE:
<223> OTHER INFORMATION: an artificially synthesized peptide

<400> SEQUENCE: 26

Arg Ser Pro Gly Ser Gly Pro Gly Ser Pro Arg Ser Pro Gly Ser Gly
1               5                   10                  15

Pro Gly Ser Pro Arg Ser
            20


<210> SEQ ID NO 27
<211> LENGTH: 72
<212> TYPE: DNA
<213> ORGANISM: Nicotiana tabacum

<400> SEQUENCE: 27

atggggagaa tgtcaatacc catgatgggt tttgtggtgt tatgtctatg ggcagtggta     60

gcagaaggat cc                                                         72


<210> SEQ ID NO 28
<211> LENGTH: 24
<212> TYPE: PRT
<213> ORGANISM: Nicotiana tabacum

<400> SEQUENCE: 28
```

Met Gly Arg Met Ser Ile Pro Met Met Gly Phe Val Val Leu Cys Leu
1 5 10 15

Trp Ala Val Val Ala Glu Gly Ser
20

<210> SEQ ID NO 29
<211> LENGTH: 4
<212> TYPE: PRT
<213> ORGANISM: Artificial Sequence
<220> FEATURE:
<223> OTHER INFORMATION: an artificially synthesized peptide

<400> SEQUENCE: 29

His Asp Glu Leu
1

<210> SEQ ID NO 30
<211> LENGTH: 91
<212> TYPE: DNA
<213> ORGANISM: Nicotiana tabacum

<400> SEQUENCE: 30
tatttaactc agtattcaga aacaacaaaa gttcttctct acataaaatt ttcctatttt 60
agtgatcagt gaaggaaatc aagaaaaata a 91

<210> SEQ ID NO 31
<211> LENGTH: 91
<212> TYPE: DNA
<213> ORGANISM: Nicotiana tabacum

<400> SEQUENCE: 31
tatttaactc agtattcaga aacaacaaaa gttcttctct acataaaatt ttcctatttt 60
agtgatcagt gaaggaaatc aagaaaaaaa g 91

<210> SEQ ID NO 32
<211> LENGTH: 256
<212> TYPE: DNA
<213> ORGANISM: Arabidopsis thaliana

<400> SEQUENCE: 32
atatgaagat gaagatgaaa tatttggtgt gtcaaataaa aagctagctt gtgtgcttaa 60
gtttgtgttt ttttcttggc ttgttgtgtt atgaatttgt ggctttttct aatattaaat 120
gaatgtaaga tctcattata atgaataaac aaatgtttct ataatccatt gtgaatgttt 180
tgttggatct cttcgcatat aactactgta tgtgctatgg tatggactat ggaatatgat 240
taaagataag actagt 256

<210> SEQ ID NO 33
<211> LENGTH: 17
<212> TYPE: PRT
<213> ORGANISM: Canine Parvovirus

<400> SEQUENCE: 33

Ser Asp Gly Ala Val Gln Pro Asp Gly Gly Gln Pro Ala Val Arg Asn
1 5 10 15

Glu

<210> SEQ ID NO 34
<211> LENGTH: 51
<212> TYPE: DNA

<213> ORGANISM: Canine Parvovirus

<400> SEQUENCE: 34
tcggacggcg cggtgcagcc ggacggcggc cagccggcgg tgcggaacga g 51

<210> SEQ ID NO 35
<211> LENGTH: 58
<212> TYPE: DNA
<213> ORGANISM: Artificial Sequence
<220> FEATURE:
<223> OTHER INFORMATION: CP-F primer

<400> SEQUENCE: 35
tggttctcct agatcctcgg acggcgcggt gcagccggac ggcggccagc cggcggtg 58

<210> SEQ ID NO 36
<211> LENGTH: 57
<212> TYPE: DNA
<213> ORGANISM: Artificial Sequence
<220> FEATURE:
<223> OTHER INFORMATION: CP-R primer

<400> SEQUENCE: 36
ccttagagct cccgggtact atcagtcctt ctcgttccgc accgccggct ggccgcc 57

<210> SEQ ID NO 37
<211> LENGTH: 30
<212> TYPE: DNA
<213> ORGANISM: Artificial Sequence
<220> FEATURE:
<223> OTHER INFORMATION: 2eB-Sal-F primer

<400> SEQUENCE: 37
ggtcacgatc atctcgtcga cgtgctcgtc 30

<210> SEQ ID NO 38
<211> LENGTH: 33
<212> TYPE: DNA
<213> ORGANISM: Artificial Sequence
<220> FEATURE:
<223> OTHER INFORMATION: PG-R primer

<400> SEQUENCE: 38
ggatctagga gaaccaggac cagaaccagg tcc 33

<210> SEQ ID NO 39
<211> LENGTH: 16
<212> TYPE: PRT
<213> ORGANISM: Porcine Parvovirus

<400> SEQUENCE: 39

Val Glu Gln His Asn Pro Ile Asn Ala Gly Thr Glu Leu Ser Ala Thr
1 5 10 15

<210> SEQ ID NO 40
<211> LENGTH: 48
<212> TYPE: DNA
<213> ORGANISM: Porcine Parvovirus

<400> SEQUENCE: 40
gtggagcagc acaaccccat caacgccggc accgagctgt ccgccacc 48

<210> SEQ ID NO 41
<211> LENGTH: 55
<212> TYPE: DNA

-continued

<213> ORGANISM: Artificial Sequence
<220> FEATURE:
<223> OTHER INFORMATION: PP-F primer

<400> SEQUENCE: 41
tggttctcct agatccgtgg agcagcacaa ccccatcaac gccggcaccg agctg 55

<210> SEQ ID NO 42
<211> LENGTH: 60
<212> TYPE: DNA
<213> ORGANISM: Artificial Sequence
<220> FEATURE:
<223> OTHER INFORMATION: PP-R primer

<400> SEQUENCE: 42
ccttagagct cccgggtact atcagtcctt ggtggcggac agctcggtgc cggcgttgat 60

<210> SEQ ID NO 43
<211> LENGTH: 22
<212> TYPE: PRT
<213> ORGANISM: Feline Immunodeficiency Virus

<400> SEQUENCE: 43

Gly Ser Trp Met Arg Ala Ile Ser Ser Trp Arg His Arg Asn Arg Trp
1 5 10 15

Glu Trp Arg Pro Asp Phe
20

<210> SEQ ID NO 44
<211> LENGTH: 66
<212> TYPE: DNA
<213> ORGANISM: Feline Immunodeficiency virus

<400> SEQUENCE: 44
ggctcctgga tgagggccat ctcctcctgg aggcacagga acaggtggga gtggaggccc 60
gacttc 66

<210> SEQ ID NO 45
<211> LENGTH: 49
<212> TYPE: DNA
<213> ORGANISM: Artificial Sequence
<220> FEATURE:
<223> OTHER INFORMATION: FIV-F primer

<400> SEQUENCE: 45
tggttctcct agatccggct cctggatgag ggccatctcc tcctggagg 49

<210> SEQ ID NO 46
<211> LENGTH: 36
<212> TYPE: DNA
<213> ORGANISM: Artificial Sequence
<220> FEATURE:
<223> OTHER INFORMATION: FIV-M primer

<400> SEQUENCE: 46
ctcccacctg ttcctgtgcc tccaggagga gatggc 36

<210> SEQ ID NO 47
<211> LENGTH: 63
<212> TYPE: DNA
<213> ORGANISM: Artificial Sequence
<220> FEATURE:
<223> OTHER INFORMATION: FIV-R primer

<400> SEQUENCE: 47

-continued ccttagagct cccgggtact atcagtcctt gaagtcgggc ctccactccc acctgttcct 60
gtg 63

<210> SEQ ID NO 48
<211> LENGTH: 8
<212> TYPE: PRT
<213> ORGANISM: Porcine epidemic diarrhea virus

<400> SEQUENCE: 48

Tyr Ser Asn Ile Gly Val Cys Lys
1 5

<210> SEQ ID NO 49
<211> LENGTH: 9
<212> TYPE: PRT
<213> ORGANISM: Porcine epidemic diarrhea virus

<400> SEQUENCE: 49

Arg Gly Pro Arg Leu Gln Pro Tyr Glu
1 5

<210> SEQ ID NO 50
<211> LENGTH: 19
<212> TYPE: PRT
<213> ORGANISM: Porcine epidemic diarrhea virus

<400> SEQUENCE: 50

Tyr Ser Asn Ile Gly Val Cys Lys Ser Ser Arg Gly Pro Arg Leu Gln
1 5 10 15

Pro Tyr Glu

<210> SEQ ID NO 51
<211> LENGTH: 57
<212> TYPE: DNA
<213> ORGANISM: Porcine epidemic diarrhea virus

<400> SEQUENCE: 51
tactccaaca tcggcgtctg caagtcctcc cggggccccc ggttgcagcc ctacgag 57

<210> SEQ ID NO 52
<211> LENGTH: 58
<212> TYPE: DNA
<213> ORGANISM: Artificial Sequence
<220> FEATURE:
<223> OTHER INFORMATION: PED-F primer

<400> SEQUENCE: 52
tggttctcct agatcctact ccaacatcgg cgtctgcaag tcctcccggg gcccccgg 58

<210> SEQ ID NO 53
<211> LENGTH: 66
<212> TYPE: DNA
<213> ORGANISM: Artificial Sequence
<220> FEATURE:
<223> OTHER INFORMATION: PED-R primer

<400> SEQUENCE: 53
ccttagagct cccgggtact atcagtcctt ctcgtagggc tgcaaccggg ggcccccgga 60
ggactt 66

<210> SEQ ID NO 54
<211> LENGTH: 14

<212> TYPE: PRT
<213> ORGANISM: Porcine Rotavirus A type

<400> SEQUENCE: 54

Thr Glu Ala Ser Thr Gln Ile Gly Asp Thr Glu Trp Lys Asn
1 5 10

<210> SEQ ID NO 55
<211> LENGTH: 16
<212> TYPE: PRT
<213> ORGANISM: Porcine Rotavirus A type

<400> SEQUENCE: 55

Thr Thr Asn Pro Ala Thr Phe Glu Glu Val Ala Lys Asn Glu Lys Leu
1 5 10 15

<210> SEQ ID NO 56
<211> LENGTH: 31
<212> TYPE: PRT
<213> ORGANISM: Porcine Rotavirus A type

<400> SEQUENCE: 56

Thr Glu Ala Ser Thr Gln Ile Gly Asp Thr Glu Trp Lys Asn Ser Thr
1 5 10 15

Thr Asn Pro Ala Thr Phe Glu Glu Val Ala Lys Asn Glu Lys Leu
20 25 30

<210> SEQ ID NO 57
<211> LENGTH: 93
<212> TYPE: DNA
<213> ORGANISM: Porcine Rotavirus A type

<400> SEQUENCE: 57
accgaggcct ccacccagat cggcgacacc gagtggaaga actccaccac caaccccgcc 60
accttcgagg aggtggccaa gaacgagaag ttg 93

<210> SEQ ID NO 58
<211> LENGTH: 76
<212> TYPE: DNA
<213> ORGANISM: Artificial Sequence
<220> FEATURE:
<223> OTHER INFORMATION: RoA7-F primer

<400> SEQUENCE: 58
tggttctcct agatccaccg aggcctccac ccagatcggc gacaccgagt ggaagaactc 60
caccaccaac cccgcc 76

<210> SEQ ID NO 59
<211> LENGTH: 36
<212> TYPE: DNA
<213> ORGANISM: Artificial Sequence
<220> FEATURE:
<223> OTHER INFORMATION: RoA7-M primer

<400> SEQUENCE: 59
ggccacctcc tcgaaggtgg cggggttggt ggtgga 36

<210> SEQ ID NO 60
<211> LENGTH: 66
<212> TYPE: DNA
<213> ORGANISM: Artificial Sequence
<220> FEATURE:
<223> OTHER INFORMATION: RoA7-R primer

<400> SEQUENCE: 60
ccttagagct cccgggtact atcagtcctt caacttctcg ttcttggcca cctcctcgaa 60
ggtggc 66

<210> SEQ ID NO 61
<211> LENGTH: 23
<212> TYPE: PRT
<213> ORGANISM: Porcine Rotavirus C type

<400> SEQUENCE: 61

Asn Ala Ala Ile Gly Ser Pro Gly Pro Gly Lys Ala Asp Gly Leu Leu
1 5 10 15

Asn Asp Asn Asn Tyr Ala Gln
20

<210> SEQ ID NO 62
<211> LENGTH: 17
<212> TYPE: PRT
<213> ORGANISM: Porcine Rotavirus C type

<400> SEQUENCE: 62

Ser Pro Ala Ser Thr Glu Thr Tyr Glu Val Val Ser Asn Asp Thr Gln
1 5 10 15

Leu

<210> SEQ ID NO 63
<211> LENGTH: 41
<212> TYPE: PRT
<213> ORGANISM: Porcine Rotavirus C type

<400> SEQUENCE: 63

Asn Ala Ala Ile Gly Ser Pro Gly Pro Gly Lys Ala Asp Gly Leu Leu
1 5 10 15

Asn Asp Asn Asn Tyr Ala Gln Ser Ser Pro Ala Ser Thr Glu Thr Tyr
20 25 30

Glu Val Val Ser Asn Asp Thr Gln Leu
35 40

<210> SEQ ID NO 64
<211> LENGTH: 123
<212> TYPE: DNA
<213> ORGANISM: Porcine Rotavirus C type

<400> SEQUENCE: 64
aacgccgcca tcggctcccc cggccccggc aaggccgacg gcctgctgaa cgacaacaac 60
tacgcccagt cctcccccgc ctccaccgag acctacgagg tggtgtccaa cgacacccag 120
ctg 123

<210> SEQ ID NO 65
<211> LENGTH: 73
<212> TYPE: DNA
<213> ORGANISM: Artificial Sequence
<220> FEATURE:
<223> OTHER INFORMATION: RoC7-F primer

<400> SEQUENCE: 65
tggttctcct agatccaacg ccgccatcgg ctcccccggc cccggcaagg ccgacggcct 60
gctgaacgac aac 73

-continued

```
<210> SEQ ID NO 66
<211> LENGTH: 69
<212> TYPE: DNA
<213> ORGANISM: Artificial Sequence
<220> FEATURE:
<223> OTHER INFORMATION: RoC7-M primer

<400> SEQUENCE: 66

caccacctcg taggtctcgg tggaggcggg ggaggactgg gcgtagttgt tgtcgttcag     60

caggccgtc                                                             69


<210> SEQ ID NO 67
<211> LENGTH: 69
<212> TYPE: DNA
<213> ORGANISM: Artificial Sequence
<220> FEATURE:
<223> OTHER INFORMATION: RoC7-R primer

<400> SEQUENCE: 67

ccttagagct cccgggtact atcagtcctt cagctgggtg tcgttggaca ccacctcgta     60

ggtctcggt                                                             69


<210> SEQ ID NO 68
<211> LENGTH: 22
<212> TYPE: PRT
<213> ORGANISM: Artificial Sequence
<220> FEATURE:
<223> OTHER INFORMATION: VP2 peptide

<400> SEQUENCE: 68

Met Ser Asp Gly Ala Val Gln Pro Asp Gly Gly Gln Pro Ala Val Arg
1               5                   10                  15

Asn Glu Arg Ala Thr Gly
            20
```

VACCINE ANTIGEN WITH INCREASED IMMUNOGENICITY

TECHNICAL FIELD

The present invention relates to a fusion protein which is useful as a vaccine, a DNA construct coding for the fusion protein, and a vector and a transformant comprising the DNA construct.

BACKGROUND ART

The use of vaccines is an effective method for disease control. However, preventive effects obtained by such methods are not sufficient in some cases. In this case, there are various possible reasons which include originally weak immunogenicity of an antigen designed as a vaccine or immunity of an individual to be vaccinated such as a newborn or an elderly person. ST, a causative toxin of coliform diarrhea, is a small molecule comprising 18 amino acids (STp (porcine type)) or 19 amino acids (STh (human type)) and having a molecular weight of approximately 2,000, and it has been known for its very low immunogenicity so far. Studies have been made to improve immunogenicity using ST as a low-immunogenicity molecular model.

Klipstein et al. (1985) (Non-Patent Document 1) created an antigen by chemically fusing STh with LTB, encapsulating the antigen in gelatin capsules, and orally administering the capsules, thereby confirming the increased antibody titers of serum IgG and small intestinal IgA. However, further improved immunogenicity has been required for practical use.

Clements (1990) (Non-Patent Document 2) induced expression of the LTB-ST fusion protein in *Escherichia coli*, purified the protein, and intraperitoneally administered the protein to mice, thereby confirming induction of the anti-ST antibody in serum. However, further increase in immunogenicity has been required.

Zhang et al. (2010) (Non-Patent Document 3) induced expression of a protein obtained by fusing LT holotoxin with ST in *Escherichia coli*, purified the protein, and intramuscularly administered the protein with an incomplete Freund's adjuvant to rabbits, thereby confirming antibody induction and induction of neutralization activity against the ST toxin. However, since the injection containing the adjuvant was administered, it has been required to further improve immunity against the antigen.

Rosales-Mendoza et al. (2011) (Non-Patent Document 4) induced expression of a fusion protein of LTB and STh in tobacco and orally administered the protein to mice, thereby confirming the increased anti-LT antibody titer. However, Rosales-Mendoza et al. did not mention the anti-ST antibody titer.

Meanwhile, the present inventors previously reported in Japanese Patent No. 5360727 (Patent Document 1) that high production of a B subunit of *Escherichia coli* heat-labile toxin (LTB) or a B subunit of Shiga toxin 2e (Stx2eB) in plants was achieved by making use of a linker (PG12) having a specific amino acid sequence. However, ability of the fusion protein serving as a vaccine or ability of the antigen in a state of being fused with a third antigen has been unclear.

PRIOR ART DOCUMENT

Patent Document

PATENT DOCUMENT 1: Japanese Patent No. 5360727

Non-Patent Documents

NON-PATENT DOCUMENT 1: Klipstein et al., Infection and Immunity (1985) 50:328-32
NON-PATENT DOCUMENT 2: Clements, Infection and Immunity (1990) 58:1159-66
NON-PATENT DOCUMENT 3: Zhang et al., Clinical and Vaccine Immunology (2010) 17:1223-31
NON-PATENT DOCUMENT 4: Rosales-Mendoza et al., Plant Cel Rep (2011) 30:1145-52

SUMMARY OF THE INVENTION

Problems to be Solved by the Invention

An object of the present invention is to provide a vaccine antigen with increased immunogenicity.

Means for Solving the Problems

As a result of intensive studies in order to achieve the above object, the inventors of the present invention found that when an antigenic peptide is bound to two or more toxin proteins selected from the group consisting of the B subunit of Shiga toxin 2e (Stx2eB), the B subunit of *Escherichia coli* heat-labile toxin (LTB), and the B subunit of cholera toxin (CTB) so as to produce a fusion protein and the protein is administered to an animal, the portion comprising the two or more toxin proteins functions as an adjuvant, thereby causing an increase in immunogenicity against the antigenic peptide in the animal body, and this fusion protein can be used as an excellent vaccine antigen. These findings have led to the completion of the present invention.

Specifically, the present invention is as follows.

(1) A fusion protein, which comprises an antigenic peptide (other than a glycoprotein 5-derived peptide of porcine reproductive and respiratory syndrome (PRRS) virus) and two or more proteins selected from the group consisting of a B subunit of Shiga toxin 2e (Stx2eB), a B subunit of *Escherichia coli* heat-labile toxin (LTB), and a B subunit of cholera toxin (CTB).

(2) A fusion protein, which comprises an antigenic peptide (other than a glycoprotein 5-derived peptide of porcine reproductive and respiratory syndrome (PRRS) virus) and an adjuvant protein, wherein the adjuvant protein comprises two or more proteins selected from the group consisting of a B subunit of Shiga toxin 2e (Stx2eB), a B subunit of *Escherichia coli* heat-labile toxin (LTB), and a B subunit of cholera toxin (CTB).

(3) The fusion protein according to (1) or (2), wherein the antigenic peptide is a bacterial toxin-derived peptide.

(4) The fusion protein according to (1) or (2), wherein the antigenic peptide is an *Escherichia coli* heat-stable enterotoxin (ST)-derived peptide.

(5) The fusion protein according to al, wherein the ST-derived peptide has an amino acid sequence having a sequence identity of 80% or more to the amino acid sequence represented by SEQ ID NO: 16.

(6) The fusion protein according to (1) or (2), wherein the antigenic peptide is a mammalian infectious virus-derived peptide.

(7) The fusion protein according to (6), wherein the mammalian infectious virus-derived peptide comprises a partial sequence of the parvovirus capsid protein VP2, feline immunodeficiency virus envelope protein gp120, porcine epidemic diarrhea virus spike protein, or rotavirus capsid protein VP7.

(8) The fusion protein according to (7), wherein the partial sequence of the parvovirus capsid protein VP2 has an amino acid sequence having a sequence identity of 80% or more to the amino acid sequence represented by SEQ ID NO: 33 or 39, the partial sequence of the feline immunodeficiency virus envelope protein gp120 has an amino acid sequence having a sequence identity of 80% or more to the amino acid sequence represented by SEQ ID NO: 43, the partial sequence of the porcine epidemic diarrhea virus spike protein has an amino acid sequence having a sequence identity of 80% or more to the amino acid sequence represented by SEQ ID NO: 50, or the partial sequence of the rotavirus capsid protein VP7 has an amino acid sequence having a sequence identity of 80% or more to the amino acid sequence represented by SEQ ID NO: 56 or 63.

(9) The fusion protein according to any one of (1) to (8), wherein said two or more proteins include Stx2eB and LTB.

(10) The control agent fusion protein according to any one of (1) to (9), wherein the Asn residue at position 73 of Stx2eB is substituted by a Ser residue.

(11) The fusion protein according to any one of (1) to (10), wherein the antigenic peptide and the B subunits of the toxins that are components of the two or more proteins are linked to each other via a peptide linker.

(12) The fusion protein according to (11), wherein the peptide linker is PG12 (SEQ ID NO: 2), PG12v2 (SEQ ID NO: 4), PG17 (SEQ ID NO: 25), or PG22 (SEQ ID NO: 26) or a peptide having an amino acid sequence having a sequence identity of 80% or more to the sequence of any thereof.

(13) The fusion protein according to any one of (1) to (12), which has an amino acid sequence represented by SEQ ID NO: 20 or 22 or an amino acid sequence having a sequence identity of 80% or more to the amino acid sequence represented by SEQ ID NO: 20 or 22.

(14) A DNA coding for the fusion protein according to any one of (1) to (13).

(15) A DNA construct comprising the DNA according to (14).

(16) A recombinant vector comprising the DNA construct according to (15).

(17) A transformant transformed with the recombinant vector according to (16).

(18) The transformant according to (17), wherein the transformant is a plant or yeast.

(19) A vaccine comprising the fusion protein according to any one of (1) to (13) or the transformant according to (17) or (18).

(20) An animal feed comprising the fusion protein according to any one of (1) to (13) or the transformant according to (17) or (18).

(21) A method for increasing immunity in a non-human mammal, which comprises administering the fusion protein according to any one of (1) to (13) or the transformant according to (17) or (18) to a non-human mammal.

Effect of the Invention

The present invention makes it possible to drastically increase immune induction efficiency and provide a vaccine against an antigen with low immunogenicity. According to the present invention, it is possible to allow a vaccine antigen to be accumulated in an edible plant such as lettuce and orally administer the vaccine antigen to an animal. Therefore, an increased productivity can be expected due to the reduction in the cost, manpower, and stress in livestock.

EMBODIMENTS FOR CARRYING OUT THE INVENTION

Figure 1:
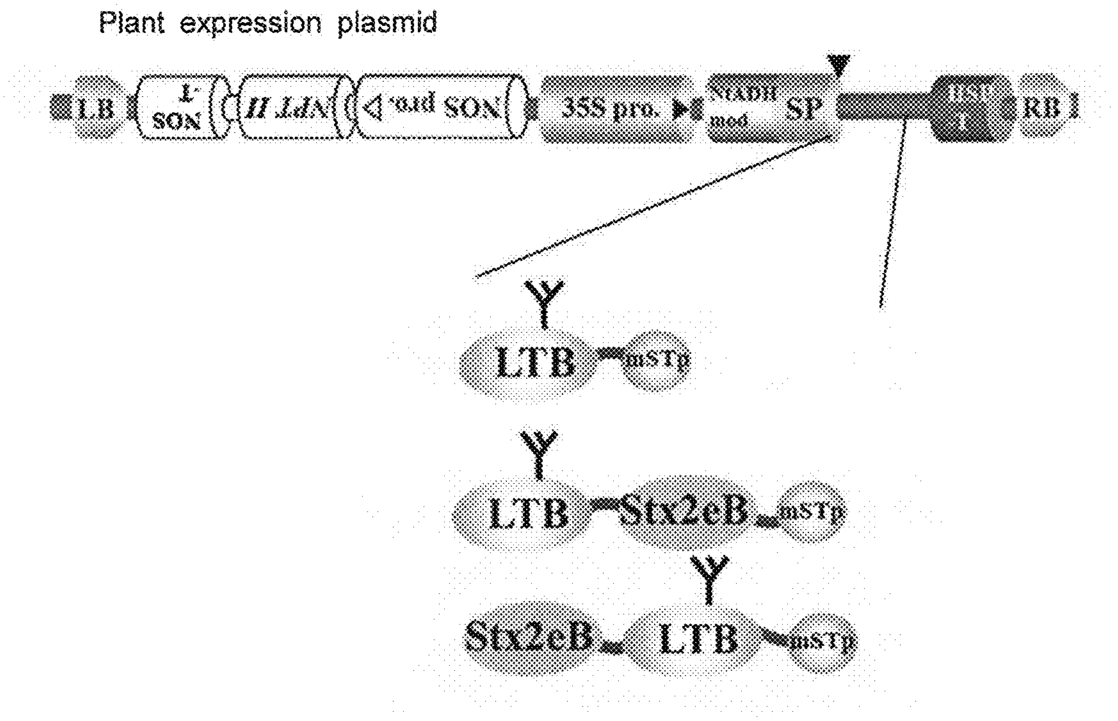
FIG. 1 illustrates a fusion protein expression cassette introduced into lettuce.

Hereinafter, the present invention is explained.

The fusion protein of the present invention comprises an antigenic peptide and an adjuvant protein, and the adjuvant protein comprises two or more proteins selected from the group consisting of a B subunit of Shiga toxin 2e (Stx2eB), a B subunit of *Escherichia coli* heat-labile toxin (LTB), and a B subunit of cholera toxin (CTB).

<Antigenic Peptide>

An antigenic peptide is not particularly limited as long as it is a peptide other than a Glycoprotein 5-derived peptide of PRRS virus, and is capable of provoking an antigen-antibody reaction in a non-human mammal administered therewith. The sequence or length thereof is not particularly limited as well. Preferably, the length of the antigenic peptide is 10 to 100 amino acids. Note that the antigenic peptide does not include either of Stx2eB, LTB, or CTB. One example of the antigenic peptide is a pathogen-derived peptide. Examples thereof include peptides produced by pathogenic bacteria such as *Escherichia coli, mycoplasma*, and *salmonella*, which are, for example, toxins (other than Stx2eB, LTB, and CTB), cell wall constituent proteins, and mammalian infectious virus-derived peptides such as capsid-derived peptides and nucleocapsid-derived peptides.

One example of an antigenic peptide is thermostable toxin (ST) that is a causative toxin of coliform diarrhea. Examples of ST include STp (porcine type) comprising 18 amino acids and STh (human type) comprising 19 amino acids. In a case in which a fusion protein is administered to a pig, STp is used. Examples of STp to be used as an antigen include a detoxified mutant (mSTp) having the amino acid sequence of SEQ ID NO: 16 (Sato et al., 1994). The antigenic peptide may have the same amino acid sequence as the amino acid sequence represented by SEQ ID NO: 16, except that one or several amino acids are substituted, deleted, inserted and/or added, as long as it is a peptide capable of provoking an antigen-antibody reaction against STp. The term "several" refers preferably to a number of from 2 to 10, more preferably from 2 to 5, and still more preferably from 2 to 3, for example. Further, STp may comprise an amino acid sequence having a sequence identity of preferably 85% or more, more preferably 90% or more, and still more preferably 95% or more to the amino acid sequence represented by SEQ ID NO: 16.

Other examples of the antigenic peptide include a neutralization epitope of the parvovirus capsid protein VP2, a neutralization epitope of the feline immunodeficiency virus envelope protein gp120, a neutralization epitope of the porcine epidemic diarrhea virus spike protein, and a neutralization epitope of the rotavirus capsid protein VP7. The virus-derived antigenic peptide is not limited to these examples, and various peptides derived from various viruses can be applied. The sequences thereof can also be determined appropriately based on alignment of known sequences or the like. It is possible to exclusively use one type of epitope. It is also possible to use a plurality of epitopes linked to each other.

The amino acid sequences of antigenic peptides of the above-mentioned neutralization epitopes of virus proteins are exemplified below.

Neutralization epitope of the canine parvovirus capsid protein VP2: SEQ ID NO: 33

Neutralization epitope of the porcine parvovirus capsid protein VP2: SEQ ID NO: 39

Neutralization epitope of the feline immunodeficiency virus envelope protein gp120: SEQ ID NO: 43

Neutralization epitope of the porcine epidemic diarrhea virus spike protein: SEQ ID NO: 50

Neutralization epitope of the rotavirus type A capsid protein VP7: SEQ ID NO: 56

Neutralization epitope of the rotavirus type C capsid protein VP7: SEQ ID NO: 63

The antigenic peptide may have the same amino acid sequence as the amino acid sequence represented by SEQ ID NO: 33, 39, 43, 50, 56, or 63, except that one or several amino acids are substituted, deleted, inserted and/or added, as long as it is a peptide capable of provoking an antigen-antibody reaction against the respective virus protein. The term "several" refers preferably to a number of from 2 to 10, more preferably from 2 to 5, and still more preferably from 2 to 3, for example. Further, the antigenic peptide may be a protein having a sequence identity of preferably 85% or more, more preferably 90% or more, and still more preferably 95% or more to the amino acid sequence represented by SEQ ID NO: 33, 39, 43, 50, 56, or 63.

<Adjuvant Protein>

An adjuvant protein includes two or more proteins selected from the group consisting of Stx2eB, LTB, and CTB. The expression "two or more" refers to preferably from 2 to 5, more preferably from 2 to 3, and further preferably 2. The expression "two or more proteins" encompasses an embodiment in which two or more toxin B subunits of a single protein selected from the group consisting of Stx2eB, LTB, and CTB are included, an embodiment in which two or more toxins of two types in total selected from the group consisting of Stx2eB, LTB, and CTB are included, or an embodiment in which Stx2eB, LTB, and CTB are included as three toxins in total.

<Stx2eB>

Shiga toxin (Stx) is a toxin protein produced by enterohemorrhagic *Escherichia coli* (EHEC, STEC), which causes edema, and classified into type 1 (Stx1) and type 2 (Stx2). Stx1 is classified into subclasses a to d, and Stx2 is classified into subclasses a to g. Stx1 is a holotoxin composed of one A subunit molecule as the toxin body and five B subunit molecules that support intestinal mucosal binding, Stx1 acts on eukaryotic cell ribosomes so as to function to inhibit protein synthesis.

The B subunit of Stx2e (Stx2eB) to be used in the present invention has, for example, the amino acid sequence represented by SEQ ID NO: 8. An amino acid sequence of the mature region (excluding a signal peptide for secretion to the periplasmic space, Ala19 to Asn87) of the Stx2e B subunit protein (GenBank Accession No. AAQ63639) is represented by SEQ ID NO: 8.

In addition, Stx2eB may have, for example, a mutant-type amino acid sequence in which Asn73 (the Asn residue at position 55 of the amino acid sequence of SEQ ID NO: 8) is substituted by a Ser residue. The amino acid sequence (Asn73Ser), in which the Asn residue at position 55 of the amino acid sequence represented by SEQ ID NO: 8 is substituted by Ser, is represented by SEQ ID NO: 10.

Stx2eB may have the same amino acid sequence as the amino acid sequence represented by SEQ ID NO: 8 or 10, except that one or several amino acids are substituted, deleted, inserted and/or added, as long as it has an adjuvant effect when it is administered as the fusion protein to an animal such as a pig. The term "several" refers preferably to a number of from 2 to 10, more preferably from 2 to 5, and still more preferably from 2 to 3, for example.

Further, Stx2eB may have an amino acid sequence having a sequence identity of preferably 85% or more, more preferably 90% or more, and still more preferably 95% or more to the amino acid sequence represented by SEQ ID NO: 8 or 10 and have an adjuvant effect when it is administered as the fusion protein to an animal such as a pig.

<LTB>

Coliform diarrhea is caused by toxin protein LT produced by enterotoxigenic *Escherichia coli* (ETEC). LT is also referred to as an "*Escherichia coli* heat-labile toxin." *Escherichia coli* heat-labile toxin (LT) is a holotoxin composed of one A subunit molecule as the toxin body and five B subunit molecules. The LT A subunit (LTA) invades cytoplasm so as to increase the intracellular cAMP concentration and activate the cell membrane chloride channel, thereby inducing water leakage in the intestine, which is a pathological condition of diarrhea. The LT B subunit (LTB) is nontoxic and involved in adhesion between the LT toxin and intestinal cells.

LTB to be used in the present invention is represented, for example, by SEQ ID NO: 12. LTB may have the same amino acid sequence as the amino acid sequence represented by SEQ ID NO: 12, except that one or several amino acids are substituted, deleted, inserted and/or added, as long as it has an adjuvant effect when it is administered as the fusion protein to an animal such as a pig. The term "several" refers preferably to a number of from 2 to 10, more preferably from 2 to 5, and still more preferably from 2 to 3, for example. The amino acid sequence represented by SEQ ID NO: 12 is registered with GenBank Accession No. AAL55672.

Further, LTB may have an amino acid sequence having a sequence identity of 85% or more, preferably 90% or more, and more preferably 95% or more to the amino acid sequence represented by SEQ ID NO: 12 and have an adjuvant effect when it is administered as the fusion protein to an animal such as a pig.

In another embodiment of the present invention, a sugar chain may be added to LTB. For example, an N-binding type sugar chain is added to the Asn residue at position 90 of LTB (corresponding to position 90 of SEQ ID NO: 12). The amino acid sequence of LTB, in which the amino acid at position 90 of SEQ ID NO: 12 is substituted by a Ser residue, is represented by SEQ ID NO: 14.

<CTB>

A cholera toxin (CT) protein is composed of one A subunit (CTA) which is the main body of the toxin and five B subunits (CTB). CTB to be used in the present invention is represented, for example, by SEQ ID NO: 6. CTB may have the same amino acid sequence as the amino acid sequence represented by SEQ ID NO: 6, except that one or several amino acids are substituted, deleted, inserted and/or added, as long as it has an adjuvant effect when it is administered as the fusion protein to an animal such as a pig. The term "several" refers preferably to a number of from 2 to 10, more preferably from 2 to 5, and still more preferably from 2 to 3, for example.

Further, CTB may have an amino acid sequence having a sequence identity of preferably 85% or more, more preferably 90% or more, and still more preferably 95% or more to the amino acid sequence represented by SEQ ID NO: 6 and have an adjuvant effect when it is administered as the fusion protein to an animal such as a pig.

Two or more toxin peptides that are components of the adjuvant portion of the fusion protein of the present invention may be two or more toxin B subunits which are arbitrarily selected from Stx2eB, LTB, and CTB. However, a preferable combination is of Stx2eB and LTB. According to the present invention, Stx2eB and LTB may be fused in an arbitrary order.

In a preferable embodiment of the present invention, an antigenic peptide such as St and two or more toxin B subunits which are arbitrarily selected from Stx2eB, LTB, and CTB are linked to each other in tandem via a peptide linker.

The peptide linker to be used in the present invention preferably has, for example, from 5 to 25, preferably from 10 to 25, more preferably from 10 to 22, and still more preferably from 12 to 22 amino acids. Further, the peptide linker to be used in the present invention preferably has a proline content of from 20% to 27%, and more preferably from 20% to 25%.

Each proline is preferably located with an interval of two or three amino acids in the peptide linker. Amino acids disposed between prolines are preferably selected from glycine, serine, and arginine. Note that not more than five and preferably not more than four amino acids other than proline may be added at either or both of ends of the peptide linker. Such preferred peptide linker is disclosed in, for example, WO2009/133882 A.

The peptide linker to be used in the present invention is preferably a peptide comprising the amino acid sequence represented by SEQ ID NO: 2 (PG12) or a peptide comprising the amino acid sequence represented by SEQ ID NO: 4 (PG12v2). A peptide comprising the amino acid sequence represented by SEQ ID NO: 25 (PG17) or a peptide comprising the amino acid sequence represented by SEQ ID NO: 26 (PG22) can also be preferably used.

The peptide linker to be used in the present invention may be a peptide having a sequence identity of preferably 80% or more and more preferably 90% to a peptide comprising the amino acid sequence represented by preferably SEQ ID NO: 2, 4, 25, or 26.

Use of using the peptide linker such as one described above makes it possible to improve stability of the fusion protein and allow the fusion protein to be highly accumulated in a host cell.

In addition, in the fusion protein to be used in the present invention, the peptide linker may be added to its C-terminus.

The fusion protein to be used in the present invention has an amino acid sequence that is represented, for example, by SEQ ID NO: 20 or 22. In a fusion protein having the amino acid sequence represented by SEQ ID NO: 20 or 22, Stx2eB, LTB, and mSTp are linked to each other in tandem via PG12.

In the fusion protein to be used in the present invention, a plant-derived secretory signal peptide or chloroplast transit signal peptide may be added to its amino terminus when the fusion protein is expressed in a plant. The term "added" as used herein is a concept including both the case where the secretory signal peptide is directly bound to the amino terminus of the fusion protein in which the subunit proteins are linked via the above-mentioned peptide, and the case where the secretory signal peptide is bound thereto via another peptide.

The secretory signal peptide is preferably derived from a plant belonging to the family Solanaceae, Brassicaceae, or Asteraceae, more preferably, a plant belonging to the genus *Nicotiana, Arabidopsis, Lactuca* or the like, and further preferably a plant derived from tobacco (*Nicotiana tabacum*), *Arabidopsis thaliana*, lettuce (*Lactuca sativa*) or the like.

Further, the secretory signal peptide is preferably derived from 3-D-glucan exohydrolase of *Nicotiana tabacum* or 38k-Da peroxidase of *Nicotiana tabacum* (GenBank Accession D 42064). The secretory signal peptide may be, for example, a peptide derived from the β-D-glucan exohydrolase of *Nicotiana tabacum* and having the amino acid sequence represented by SEQ ID NO: 28. The nucleotide sequence of DNA which codes for the β-D-glucan exohydrolase of *Nicotiana tabacum* is represented, for example, by the sequence of SEQ ID NO: 27.

Preferred examples of the chloroplast transit signal peptide are described in, for example, WO2009/004842 A and WO2009/133882 A.

In the fusion protein to be used in the present invention, a signal peptide such as an endoplasmic reticulum retention signal peptide or a vacuolar transport signal peptide may be added to its carboxyl terminus in a case in which, for example, the fusion protein is expressed in a plant. The term "added" as used herein is a concept including both the case where the signal peptide is directly bound to the carboxyl terminus of the fusion protein, and the case where the signal peptide is bound thereto via another peptide. In the present specification, a hybrid protein in which the secretory signal peptide is added to its amino terminus and the endoplasmic reticulum retention signal peptide is added to the carboxyl terminus is also referred to as an endoplasmic reticulum-type (ER) hybrid protein, and a DNA construct coding for the endoplasmic reticulum-type fusion protein is also referred to as an endoplasmic reticulum-type DNA construct. Many studies have been reported that the endoplasmic reticulum-type fusion protein is efficiently accumulated in eukaryotes.

In the fusion protein to be used in the present invention, the endoplasmic reticulum retention signal peptide is preferably added to its carboxyl terminus. Preferred endoplasmic reticulum retention signal peptides are disclosed, for example, in WO 2009/004842 A and WO 2009/133882 A. Among these, HDEL sequence (SEQ ID NO: 29) may be used.

Other preferred vacuolar transport signal peptides are disclosed, for example, in WO 2009/004842 A and WO 2009/133882 A.

The fusion protein to be used in the present invention can be synthesized chemically or may be produced by genetic engineering.

In the case of producing the fusion protein by genetic engineering, a DNA construct comprising DNA coding for a fusion protein is used. The DNA construct to be used in the present invention includes DNA, in which DNA coding for an antigenic peptide such as ST is linked to DNA coding for Stx2eB and DNA coding for LTB, DNA coding for Stx2eB and DNA coding for CTB, or DNA coding for LTB and DNA coding for CTB in tandem via DNA coding for the above-mentioned linker peptide. DNA coding for the linker peptide is represented, for example, by SEQ ID NO: 1 (PG12) or SEQ ID NO: 3 (PG12v2). Examples of DNA coding for Stx2eB include DNA coding for Stx2eB (Asn73) (SEQ ID NO: 7) and DNA coding for Stx2eB (Asn73Ser) (SEQ ID NO: 9). Examples of DNA coding for LTB include DNA coding for LTB (Asn90) (SEQ ID NO: 11) and DNA coding for LTB (Asn90Ser) (SEQ ID NO: 13). DNA coding for CTB is, for example, DNA coding for the nucleotide sequence of SEQ ID NO: 5.

DNA coding for an antigenic peptide can be obtained based on known information by a technique such as PCR. DNA coding for mSTp is, for example, DNA having the nucleotide sequence of SEQ ID NO: 15.

The above-mentioned DNA coding for an antigenic peptide, DNA coding for a linker peptide, and toxin B subunit DNA are linked in frame without each termination codon.

DNAs coding for Stx2eB, LTB, and CTB can be obtained by a general gene engineering technique based on, for example, the nucleotide sequences of SEQ ID NOS: 7, 9, 11, 13, and 5. Specifically, a cDNA library is prepared using a bacterium producing each toxin in accordance with an ordinary method. A desired clone is selected from the library using probes produced based on the above mentioned nucleotide sequence. In addition, it is also possible to synthesize DNA by chemical synthesis based on the above mentioned nucleotide sequence, PCR with the use of 5'-terminal and 3'-terminal nucleotide sequences as primers and genomic DNA as a template, or the like.

By linking these DNAs to DNA coding for a linker by a known technique, DNA coding for a fusion protein can be obtained.

The DNA coding for the fusion protein to be used in the present invention is represented, for example, by SEQ ID NO: 19 or 21.

The DNA coding for the fusion protein may also be a DNA which hybridizes with the DNA having the nucleotide sequences of SEQ ID NO: 19 or 21 under stringent conditions. The term "stringent conditions" refers to the conditions in which a so-called specific hybrid is formed, but not a non-specific hybrid. Examples of the stringent conditions include those in which two DNAs having a high sequence identity to one another, preferably two DNAs having a sequence identity of 80% or more, more preferably 90% or more, and particularly preferably 95% or more to one another are hybridized with each other, but two DNAs having a sequence identity lower than that described above are not hybridized. The conditions may be, for example: 2×SSC (330 mM NaCl, 30 mM citric acid) at 42° C.; and preferably: 0.1×SSC (330 mM NaCl, 30 mM citric acid) at 60° C.

In the DNA coding for the fusion protein, it is also preferred that a codon(s) corresponding to an amino acid(s) constituting the fusion protein be modified as appropriate such that the amount of the translated hybrid protein is increased depending on the host cell in which the fusion protein is produced. The modification of the codon(s) can be carried out, for example, by referring to a method disclosed by Kang et al., (2004). Further, examples of the modification method include a method for selecting a codon(s) frequently used in the host cell, a method for selecting a codon(s) having a high GC content, and a method for selecting a codon(s) frequently used in housekeeping genes in the host cell.

In the DNA construct to be used in the present invention, it is preferred that the DNA coding for the fusion protein be operably-linked to an enhancer. The term "operably" as used herein means that, when the DNA construct to be used in the present invention is inserted into a vector including a suitable promoter, and the vector is introduced into a suitable host cell, the fusion protein is produced in the host cell. Further, the term "linked" refers to both the case in which two DNAs are directly linked and the case in which two DNAs are linked via another nucleotide sequence.

Examples of the enhancer include Kozak sequence and a 5'-untranslated region of an alcohol dehydrogenase gene derived from a plant. In the case of expression in a plant, preferably, the DNA coding for the hybrid protein is operably-linked to the 5'-untranslated region of an alcohol dehydrogenase gene derived from a plant.

The 5'-untranslated region of an alcohol dehydrogenase gene refers to a region including a nucleotide sequence from the transcription start site before the translation start site (ATG, methionine), of a gene coding for the alcohol dehydrogenase. The above-mentioned region may be any region as long as it is derived from a plant. However, it is preferably derived from a plant belonging to the family Solanaceae, Brassicaceae, or Asteraceae, more preferably, derived from tobacco (*Nicotiana tabacum*), *Arabidopsis thaliana*, lettuce (*Lactuca sativa*), or the like.

The 5'-untranslated region of an alcohol dehydrogenase gene may be, for example, the 5'-untranslated region of an alcohol dehydrogenase gene (NtADH 5'UTR) (SEQ ID NO: 30) derived from tobacco (*Nicotiana tabacum*). By using the NtADH 5'UTR region in which three bases upstream of the translation start site are modified (NtADHmod 5'UTR) (SEQ ID NO: 31), in particular, a higher translation level can be expected.

Methods for obtaining the 5'-untranslated region of an alcohol dehydrogenase gene derived from a plant are described, for example, in JP 2012-19719 A and WO 2009/133882 A.

The DNA constructs to be used in the present invention can be prepared by a common genetic engineering technique, which includes the following procedures: digesting each of the DNAs, such as the 5'-untranslated region of an alcohol dehydrogenase gene derived from a plant, a DNA coding for the secretory signal peptide derived from a plant, the DNA coding for the fusion protein, and a DNA coding for the endoplasmic reticulum retention signal peptide, with a suitable restriction enzyme; and ligating the resulting fragments with a suitable ligase.

The recombinant vector to be used in the present invention is characterized by comprising the DNA construct. The recombinant vector to be used in the present invention may be any vector in which the DNA coding for the fusion protein is inserted into the vector such that the DNA can be expressed in a host cell into which the vector is introduced. The vector is not particularly limited as long as it can be replicated in a host cell, and examples thereof include a plasmid DNA, a viral DNA and the like. Further, it is preferred that the vector include a selective marker such as a drug resistance gene. The plasmid DNA can be prepared from *Escherichia coli* or *Agrobacterium tumefaciens* by the alkaline extraction method (Birnboim, H. C. & Doly, J. (1979) Nucleic acid Res 7: 1513) or a variation thereof. Commercially available plasmids such as pBI121, pBI101, pIG121Hm and the like can also be used. As the viral DNA, pTB2 (Donson et al., 1991) and the like can be used, for example (see Donson J., Kerney C M., Hilf M E., Dawson W O. Systemic expression of a bacterial gene by a tobacco mosaic virus-based vector. Proc. Natl. Acad. Sci. (1991) 88: 7204-7208).

A promoter to be used in the vector can be selected as appropriate depending on the type of host cell into which the vector is introduced. Preferred examples of the promoter include a cauliflower mosaic virus 35S promoter (Odell et al. 1985 Nature 313:810), a rice actin promoter (Zhang et al. 1991 Plant Cell 3:1155), a corn ubiquitin promoter (Cornejo et al. 1993 Plant Mol. Biol. 23:567), and the like. Further, a terminator to be used in the vector may also be selected as appropriate depending on the type of host cell into which the vector is introduced. Preferred examples of the terminator include a nopaline synthase gene transcription terminator, a cauliflower mosaic virus 35S terminator, *Arabidopsis thaliana* heat shock protein 18.2 gene terminator (HSP-T), and the like. A preferred terminator to be used in the present invention is, for example, HSP-T represented by SEQ ID NO: 32.

The recombinant vector to be used in the present invention can be prepared, for example, as follows.

First, the above-mentioned DNA construct is digested with a suitable restriction enzyme, or a restriction enzyme site is added to the DNA construct by PCR. Subsequently, the resulting DNA construct is inserted into the restriction enzyme site or multicloning site of a vector.

The transformant to be used in the present invention is characterized by being transformed with the above mentioned recombinant vector. The host cells to be used for the transformation may be eukaryotic cells or prokaryotic cells.

The eukaryotic cells are preferably plant cells as well as mammalian cells, yeast cells, and insect cells, and among these, particularly preferred are cells of plants belonging to the family Asteraceae (including those belonging to the genus *Lactuca*, for example), Solanaceae, Brassicaceae, and Chenopodiaceae. Further, preferred eukaryotic cells are cells of plants belonging to the genus *Lactuca*, particularly lettuce (*Lactuca sativa*) cells. When the lettuce cells are used as the host cells, a cauliflower mosaic virus 35S RNA promoter, or the like can be used in the vector.

The prokaryotic cells may be cells of *Escherichia coli, Agrobacterium tumefaciens*, and the like.

The transformant to be used in the present invention can be prepared by introducing the vector to be used in the present invention into host cells, using a common genetic engineering technique. Examples of the method which can be used to introduce the vector include: a method using *Agrobacterium tumefaciens* (Hood, et al., 1993, Transgenic, Res. 2: 218, Hiei, et al., 1994 Plant J. 6: 271), an electroporation method (Tada, et al., 1990, Theor. Appl. Genet, 80: 475), a polyethylene glycol method (Lazzeri, et al., 1991, Theor. Appl. Genet. 81: 437), a particle gun method (Sanford, et al., 1987, J. Part. Sci. tech. 5: 27), a polycation method (Ohtsuki, et al., FEBS Lett. 1998 May 29; 428 (3):235-40.), and the like.

After introducing the vector to be used in the present invention into the host cells, the above mentioned transformant can be selected based on the phenotype of the selective marker. Further, the fusion protein can be produced by culturing the selected transformant. The culture medium and conditions to be used in the culture can be selected as appropriate, depending on the type of the transformant.

In cases where plant cells are used as the host cells, culture of selected plant cells in accordance with a conventional method allows for regeneration of a plant body, and for accumulation of the fusion protein inside the plant cells or outside the cell membrane of the plant cells. The method varies depending on the type of plant cells to be used, and examples thereof include the method for Visser et al. (Theor. Appl. Genet 78: 594 (1989)) for potato cells, and the method for Nagata and Takebe (Planta 99: 12 (1971)) for tobacco cells.

In the case of lettuce (*Lactuca* saliva), for example, the regeneration of a shoot is possible in MS culture medium containing 0.1 mg/l of NAA (naphthaleneacetic acid), 0.05 mg/l of BA (benzyladenine) and 0.5 g/l of polyvinylpyrrolidone, and the rooting of the regenerated shoot can be achieved by culturing it in ½ MS culture medium containing 0.5 g/11 of polyvinylpyrrolidone.

Further, when a seed is collected from the thus regenerated plant body, and the seed is seeded and grown by an appropriate method, a plant body capable of producing the fusion protein can be obtained, and the thus obtained plant body is also included in the above mentioned transformant.

*Agrobacterium tumefaciens* infects a plant through a wound in the plant, and carries a large extrachromosomal element referred to as a Ti (tumor-inducing) plasmid. Many laboratories have devoted considerable effort over several years to develop an *Agrobacterium* system, and as a result, it has become possible to transform various types of plant tissues as desired. Representative plants transformed by the above-mentioned technique include tobacco, tomato, sunflower, cotton, rapeseed, potato, poplar, soybean, strawberry, rice, and the like.

It has been demonstrated that various species of plants can be regenerated from tissues transformed with *Agrobacterium tumefaciens*. Examples of such plants include sunflower, tomato, white clover, rapeseed, cotton, tobacco, potato, corn, strawberry, rice, and many other kinds of vegetable crops.

In the present invention, it is preferred that an edible plant such as lettuce, as described above, be transformed with an *Agrobacterium* Ti vector.

The vaccine according to the present invention may contain the fusion protein, and it may contain a transformant obtained by DNA transformation. The vaccine according to the present invention may include the entire or a part of the transformant containing the fusion protein. Further, the transformant can be used as it is, or it can be dried, crushed, and/or the like before being used. It is also possible to add any of other adjuvants which enhance the immunogenicity of the fusion protein to the vaccine according to the present invention. In general, aluminum hydroxide or an adhesin of

*Escherichia coli* such as flagellin of *Escherichia coli* is used as an adjuvant in consideration of safety.

By administering the vaccine according to the present invention, it is possible to increase immunity against an antigenic peptide, which is expected to be effective for preventing a disease caused by a pathogen that is the origin of the antigenic peptide.

For example, in a case in which ST is used for an antigenic peptide, it can be effective for preventing coliform diarrhea.

The method for increasing immunity according to the present invention is characterized by administering a transformant such as a plant body transformed with the above-mentioned DNA construct, or a dried product or a ground product thereof, to an animal. Subjects of the administration include pigs, cattle, chickens, sheep, goats, dogs, cats, other non-human mammals, and fish. In the case of pigs, examples of target diseases include brucellosis, anthrax, tetanus, swine erysipelas, swine dysentery, *salmonellosis*, colibacillosis, atrophic rhinitis, *Actinobacillus* diseases, *mycoplasma* infections, porcine transmissible gastroenteritis, porcine epidemic diarrhea, swine influenza, Japanese encephalitis, Aujeszky's disease, foot-and-mouth disease, swine vesicular disease, hog cholera, swine leukemia, porcine reproductive and respiratory syndrome, rotavirus, ascariasis, metastrongylus apri infection, toxoplasmosis, and coccidiosis. Examples of diseases targeting cattle include contagious bovine pleuropneumonia, anthrax, hemorrhagic septicemia, brucellosis, tuberculosis, *salmonellosis*, tetanus, rinderpest, foot-and-mouth disease, epidemic encephalitis, rabies, vesicular stomatitis, Rift Valley disease, Johne's disease, bluetongue, Akabane disease, Chuzan disease, lumpy skin disease, bovine viral diarrhea, bovine leukemia, piroplasmosis, and anaplasmosis. Examples of diseases targeting chickens include *salmonellosis*, mycoplasmosis, chicken colibacillosis, *haemophilus*, Newcastle disease, highly pathogenic avian influenza, highly virulent contagious chicken bronchitis, fowlpox, chicken encephalomyelitis, and coccidiosis. Examples of diseases targeting goats include anthrax, brucellosis, tuberculosis, Chuzan disease, foot and mouth disease, and Akabane disease. Examples of diseases targeting dogs include leptospirosis, bacterial enteritis, rabies, parvovirus infection, distemper virus infection, canine infectious bronchitis (kennel cough), coronavirus infections, herpesvirus infections, and babesiosis. Examples of diseases targeting cats include feline hemoplasma infection, rickettsial infection, rabies, feline leukemia virus infection, feline herpesvirus infection, feline immunodeficiency virus (FIV) infection, feline calicivirus infection, feline viral rhinotracheitis (FVR), and feline filariasis.

Examples of diseases targeting fish include *streptococcus* infection, *Vibrio* disease, and iridovirus infection.

In a case in which the vaccine according to the present invention is administered to pigs, it is possible to administer the vaccine to, for example, pigs ranging from those in the suckling period to those aged 120 days and preferably in pigs ranging from those in the suckling period to those aged 90 days. It is also preferable to administer the vaccine to mother pigs around the breeding period. Examples of the immunization method include a method in which a plant body transformed with the above mentioned DNA construct is administered to a mother pig and feeding piglets with milk containing an antibody produced by the mother and a method in which a plant body transformed with the DNA construct is administered to piglets ranging from those in the suckling period to those aged 90 days so as to directly immunize the piglets.

Examples of the method for administering the vaccine according to the present invention to a pig include a method in which a plant body transformed with the DNA construct, or a dried product or a ground product thereof, is mixed with a feed to be fed to a pig; a method in which the plant body, or the dried or ground product thereof, is administered to a pig by nasal drops; and the like. It is preferred that the vaccine according to the present invention be administered for a plurality of times at certain intervals. For example, the agent may be administered every four to seven days for a total of two to three times.

Examples of the present invention will now be described below. However, the present invention is not limited by the following Examples.

EXAMPLES

Example 1

<Construction of Vaccine Genes for *Escherichia coli* Expression>

The followings were used as candidate vaccine antigens: 1) a nontoxic B subunit of a heat-labile toxin produced by enterotoxigenic *Escherichia coli* (LTB:SEQ ID NO: 12); 2) a detoxified mutant of an STp toxin produced by enterotoxigenic *Escherichia coli* (NTFYCCELCCNPLCAGCY (SEQ ID NO: 16), hereinafter referred to as "mSTp") (Sato et al., 1994); and 3) a nontoxic B subunit of Shiga toxin 2e produced by enterohemorrhagic *Escherichia coli* (Stx2eB). Sugar-chain-free Stx2eB (with a substitution of asparagine at position 73 from the N-terminus by serine) (SEQ ID NO: 10) was used herein as Stx2eB. DNA coding for mSTp was amplified using STpA13L-F (5'-gatcc aac acc ttc tac tgc gag ttg tgc tgc-3': SEQ ID NO: 23) and STpA13L-R (5'-gatct gta gca gcc ggc gca caa ggg gtt gca caa ctc: SEQ ID NO: 24).

LTB-mSTp (SEQ ID NO: 18) was constructed by fusing LTB and mSTp via a PG12 linker (Matsui et al, Transgenic Res, 2011, 20:735-48:SEQ ID NO: 2), and LTB-Stx2eB-mSTp (SEQ ID NO: 20) and Stx2eB-LTB-mSTp (SEQ ID NO: 22) were constructed by fusing LTB and Stx2eB in that order or the reverse order and further fusing mSTp with each of the C-terminus. Proximal-sequence-modified NtADH 5'-UTR (SEQ ID NO: 31) and a long-chain-type AtHSP terminator (Matsui et al., Plant Biotech., 2014, 31:191-194: SEQ ID NO: 32) were used. In addition, tobacco-derived J-D-glucan exohydrolase secretory signal peptide-coding sequence (SEQ ID NO: 27) was used so as to achieve high accumulation of proteins as combined vaccine antigen candidates. Each constructed gene cassette was introduced into a binary vector PRI909 (TAKARA) for use in transformation of lettuce (FIG. 1).

<Gene Transfer into Lettuce Using *Agrobacterium tumefaciens*>

Green wave (Takii Co., Ltd.), which is a lettuce (*Lactuca sativa* L.) cultivar, was seeded aseptically in MS culture medium [½× mixed salts for Murashige and Skoog medium (MS salts, Wako Pure Chemical Industries, Ltd.), 1× Murashige and Skoog vitamin solution (MS vitamins, Sigma-Aldrich), 3% sucrose, 0.8% agar, pH 5.8]. After the seeding, a true leaf was collected on days 10 to 16, and a section of approximately 5 mm square was cut out. After immersing the section in a suspension of *Agrobacterium tumefaciens* (EHA105) carrying a binary plasmid (pRI909) containing each of the vector constructs for ten minutes, the section was placed in a co-culture medium [1×MS salts, 1×MS vitamins, 0.05 mg/l 6-benzylaminopurine (BA), 0.1 mg/l I-naphthylacetic acid (NAA), 0.1 M acetosyringone, 3% sucrose, 0.8% agar, pH 5.8], and cultured for two days at 25° C. in the dark. After washing with sterilized water, the section was placed on a selection medium [1×MS salts, 1×MS vitamins, 0.05 mg/l BA, 0.1 mg/l NAA, 0.5 g/l polyvinylpyrrolidone (PVP), 50 mg/l kanamycin (Km), 250 mg cefotaxime (Cef), 3% sucrose, 0.8% agar, pH 5.8], and cultured at 25° C. under fluorescent light (2,000 to 3,000 lux). Thereafter, the section was transferred to a new selection medium every three to four days (twice a week) until adventitious buds were obtained. Redifferentiated individuals formed from the adventitious buds were transplanted to a rooting medium [½×MS salts, 1×MS vitamins, 0.5 g/l PVP, 250 mg Cef, 3% sucrose, 0.8% agar, pH 5.8], and cultured under the same conditions. Thereafter, the redifferentiated individuals were transplanted to a new rooting medium every three to four days (twice per week). The rooted redifferentiated individuals were transplanted to a pot and cultured under the same conditions.

<Extraction of Proteins from Lettuce>

The extraction of proteins was carried out in accordance with the TCA-acetone method (Shultz et al. Plant Mol Biol Rep, 2005, 23:405) using true leaves of the transgenic lettuces which had been frozen with liquid nitrogen and stored at −80° C. A quantity of 100 to 200 mg of each lettuce sample was crushed using Tissue Lyzer II (QIAGEN), and to the resultant, TCA-acetone (10% trichloroacetic acid, 90% acetone, and 0.07% 2-mercaptoethanol) in an amount five times the amount of the sample was added. The resultant was mixed and left to stand for one hour at −20° C., and then centrifuged at 16,000×g and at 4° C. for 30 minutes, followed by removing the supernatant, thereby obtaining precipitates containing proteins. Further, in order to remove impurities, acetone/BME (100% acetone, 0.07% 2-mercaptoethanol) in an amount five times the amount of the sample was added, and the resultant was mixed and centrifuged at 16,000×g and at 4° C. for ten minutes, followed by removing the supernatant. The above described operation to remove impurities was carried out for two more times. The resulting precipitates were dried under reduced pressure and suspended in extraction I buffer [0.5 M sodium chloride, 5 mM imidazole, 6M urea, 20 mM tris (hydroxymethyl)aminomethane (Tris)-HCl, pH 7.9] in an amount two times the amount of the sample. The resulting suspension was centrifuged at 16,000×g and at 4° C. for ten minutes, and the supernatant was collected, thereby obtaining a protein solution. The concentration of the proteins was measured using Protein Assay Kit II (Bio-Rad).

<Western Analysis>

The thus obtained protein solution was placed in a microtube in an appropriate amount, and the same amount of sample buffer (EZ Apply, manufactured by ATTO) was added thereto. The resultant was then mixed and heated for five minutes in boiling water to carry out SDS treatment of the sample. The purified LTB+ was used as a standard reference material when carrying out the quantification of proteins. The purified LTB+ was repeatedly diluted two-fold using the extraction I buffer to prepare a dilution series, and the dilution series was used as a standard.

The electrophoresis (SDS-PAGE) of proteins was carried out using an electrophoresis tank (Mini Protean Tetracell) and Mini Protean TGX-gel (BIO RAD). An electrophoresis buffer (EZ Run, manufactured by ATTO) was added, 5 μl of the SDS-treated sample was applied to a well, and the electrophoresis was carried out at a constant voltage of 200 V for 40 minutes.

After the electrophoresis, the blotting of the gel was carried out using a Trans-Blot Transfer Pack (BIO RAD) and Trans-Blot Turbo (BIO RAD). The blotted membrane was immersed in a blocking solution (TBS-based, pH 7.2, Nakalai Tesque, Inc.), followed by shaking at room temperature for one hour, or left to stand at 4° C. for 16 hours. The membrane was then shaken in TBS-T (137 mM sodium chloride, 2.68 mM potassium chloride, 1% polyoxyethylene sorbitan monolaurate, 25 mM Tris-HCl, pH 7.4) at room temperature for five minutes, and the shaking was repeated for a total of three times to carry out washing. For LTB protein detection, antiserum Rabbit-Antiserum Anti-LTp 991109 (inactive) (0.1% $NaN_3$)AO, which was diluted 10,000-fold with TBS-T, was used. The membrane was immersed in the diluted solution and shaken at room temperature for two hours, thereby conducting an antigen-antibody reaction. The shaking in TBS-T at room temperature for five minutes was repeated for a total of three times to carry out washing. As a secondary antibody, the Anti-Rabbit IgG, AP-linked Antibody (Cell Signaling TECHNOLOGY), which was diluted 10,000-fold with TBS-T, was used. The membrane was immersed in the diluted solution and shaken at room temperature for one hour, thereby conducting an antigen-antibody reaction. The shaking in TBS-T at room temperature for five minutes was repeated for a total of three times to carry out washing. To carry out a chromogenic reaction with alkaline phosphatase, the washed membrane was immersed in a chromogenic solution (0.1 M sodium chloride, 5 mM chlorinated magnesium, 0.33 mg/ml nitro blue tetrazolium, 0.33 mg/ml 5-bromo-4-chloro-3-indolyl-phosphoric acid, 0.1 M Tris-HCl, pH 9.5), followed by shaking at room temperature for seven minutes. The membrane was then washed with distilled water and dried at normal temperature.

The stained membrane was imaged at a resolution of 600 dpi using a scanner (PM-A900, Epson), and the quantification of the LTB proteins was carried out using an image analysis software (CS Analyzer ver. 3.0, ATTO).

<Oral Immunization of Mice with Recombinant Lettuce>

Figure 2:
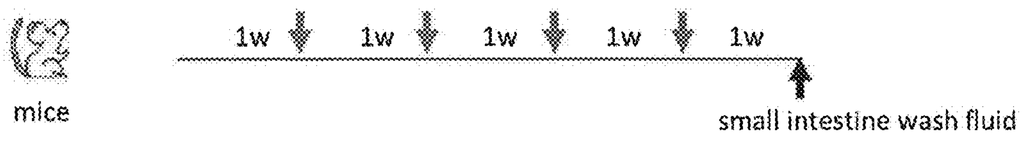
FIG. 2 is a diagram illustrating the scheme of oral administration of vaccine lettuce.

Six-Week-old female Balb/c mice were introduced, habituated, and subjected to blood sampling before immunization. Immunization was initiated when they became eight weeks old. A recombinant lettuce powder containing LTB in an amount corresponding to 730 gig was suspended in physiological saline. The resulting suspension was orally administered using a gastric feeding needle. Oral administration was performed every seven days for four times in total (FIG. 2). A piece of 5 cm in length was prepared by cutting the ileocecal region of the small intestine, followed by washing with 5 mL of PBS to obtain intestinal wash fluid. The fluid was stored at −80° C. until use, and a protease inhibitor was added thereto upon antibody titer measurement.

<Antibody Titer Measurement>

Antibody titer measurement was carried out using an ELISA plate (Maxisorp: Nunc) on which a solid phase of a 2.5 μg/mL antigen was formed at 100 μL/well. As an antigen, purified detoxified Stx2eB was used for the anti-Stx2eB antibody, purified LTp was used for the anti-LTp antibody, and a synthetic STp peptide was used for the anti-mSTp antibody. For test serum, a two-fold dilution series was prepared using a diluent containing bovine serum albumin (0.1% w/v) and applied to the ELISA plate. Detection was carried out by a chromogenic method using, as a secondary antibody, a horseradish peroxidase (HRP)-labeled antibody and, as a substrate, hydrogen peroxide, and ABTS (2,2'-azino-bis (3-ethylbenzthiazoline-6-sulphonic acid)). Absorbance two-fold or greater the average of absorbance of a diluted solution used as a negative control was determined to be a positive antibody titer, and the maximum dilution rate for the positive antibody titer was determined to be the antibody titer of the serum. In a case in which an antibody titer was detected for unimmunized serum, a value divided by the antibody titer of the unimmunized serum was determined to be the antibody titer of the serum.

<Results>

(1) Production of Gene Recombinant Plants

Gene recombinant lettuce was produced using the construct illustrated in FIG.

Figure 3:
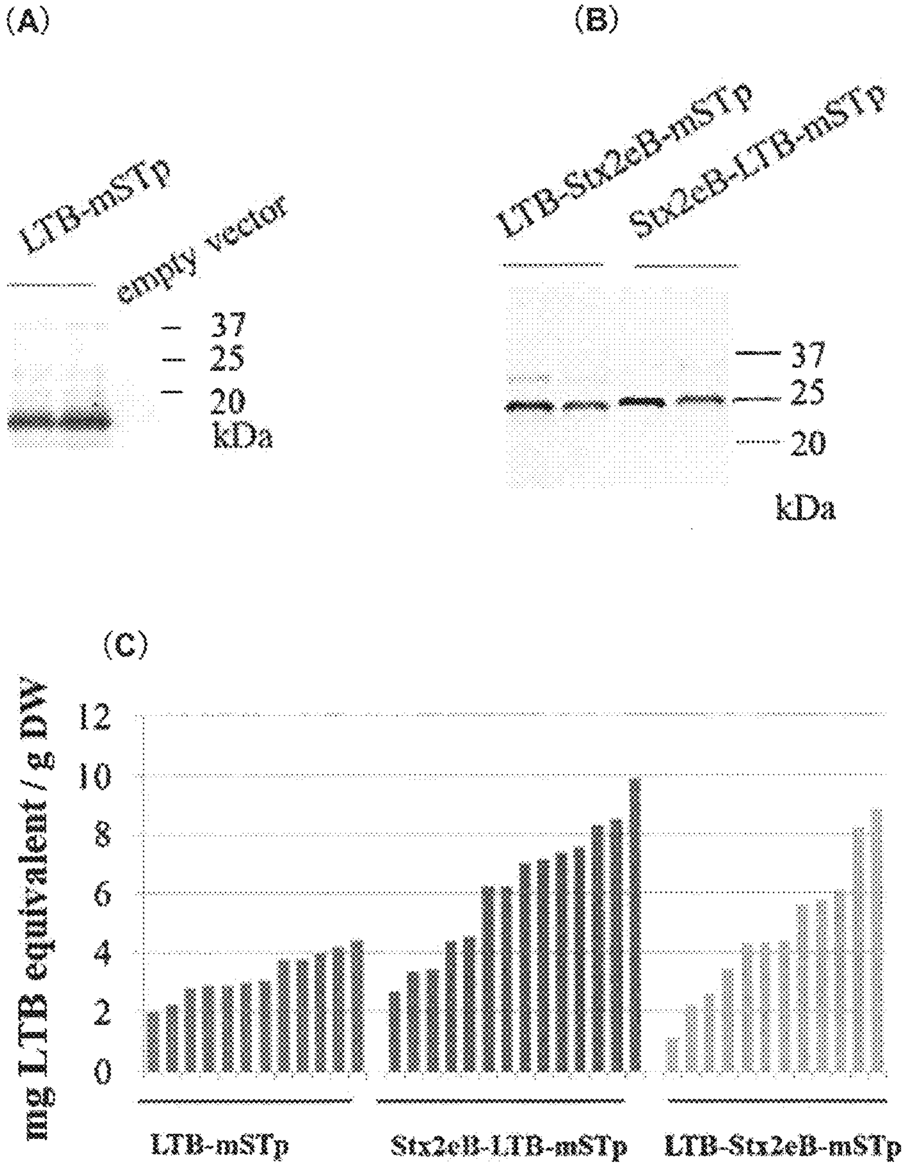
FIG. 3 is an image of the expression of a vaccine protein in lettuce (photographic image): (A) Western analysis of LTB-mSTp; (B) Western analysis of LTB-Stx2eB-mSTp and Stx2eB-LTB-mSTp; and (C) the amount of accumulation in lettuce.

1. For the lettuce transfected with LTB-mSTp, a band was detected at a position of an estimated molecular weight (approximately 15 kda) (FIG. 3A). For the lettuce transfected with LTB-Stx2eB-mSTp or Stx2eB-LTB-mSTp, a band was detected at a position of an estimated molecular weight (approximately 24 kda) (FIG. 3B). In addition, signals, which were presumed to be derived from glycosylation of LTB, were also detected. FIG. 3C shows the accumulated amount of each combination vaccine antigen.

(2) Oral Immunization of Mice with the Gene Recombinant Vaccine Plants

Figure 4:
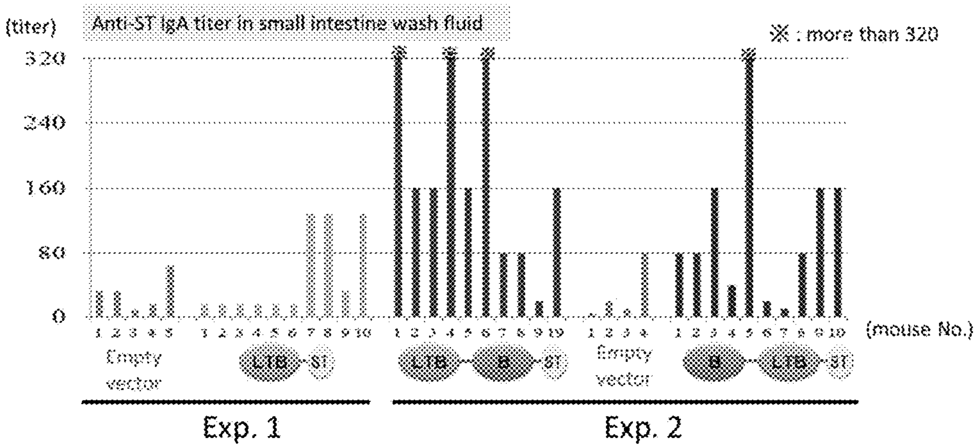
FIG. 4 is a graph showing anti-STp IgA antibody titers in mice administered with vaccine lettuce.

The gene recombinant lettuce produced in (1) was freeze-dried and crushed. The resulting powder was orally administered to mice. The amount of the powder administered was adjusted in terms of LTB equivalent. Small intestine wash fluid was collected upon autopsy, and the anti-STp IgA antibody titer was measured. As a result, an increase in the antibody titer was observed at a rate of 3 out of 10 individuals in the LTB-mSTp administration group. Meanwhile, obvious antibody induction was confirmed in 7 individuals and 4 individuals in the LTB-Stx2eB-mSTp administration group and the Stx2eB-LTB-mSTp administration group, respectively (FIG. 4). Further, the antibody titer in either the LTB-Stx2eB-mSTp group or the Stx2eB-LTB-mSTp group was greater than the LTB-mSTp group.

Example 2

<Gene Construction>

Vaccine antigens for the following diseases were each fused with LTB-Stx2eB. First, the LTB-Stx2eB fusion gene was introduced into pYES2 (Invitrogen).

As a canine parvovirus neutralization epitope, a sequence (SDGAVQPDGGQPAVRNE: SEQ ID NO: 33) derived from a capsid protein VP2 neutralization epitope was used (Casal et al., Journal of Virology, 1995 69, 7274-7277). This epitope has a sequence that is highly maintained among cell lines. For example, the DNA sequence thereof is represented by 5'-tcggacggcgcggtgcagccggacggcggccagccggcggtgcggaacgag-3' (SEQ ID NO: 34).

Figure 5:
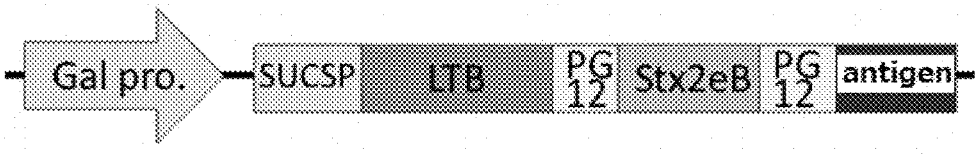
FIG. 5 is a diagram illustrating an expression cassette of a fusion protein introduced into yeast.

DNA of the neutralization epitope region was prepared by conducting annealing of a CP-F primer (5'-TGGTTCTCCTAGATCC TCG GAC GGC GCG GTG CAG CCG GAC GGC GGC CAG CCG GCG GTG-3': SEQ ID NO: 35) and a CP-R primer (5'-CCTTAGAGCTCCCGGGTACTATCAGTCCTT CTC GTT CCG CAC CGC CGG CTG GCC GCC-3': SEQ ID NO: 36) and conducting an elongation reaction by DNA polymerase. In addition, a fragment corresponding to the downstream region of Stx2eB was amplified by PCR using a 2eB-Sal-F primer (5'-GGTCACGATCATCTCGTCGACGTGCTCGTC-3': SEQ ID NO: 37) and a PG-R primer (5'-GGATCTAGGAGAACCAGGACCAGAACCAGGTCC-3': SEQ ID NO: 38) and, as a template, pYES2 LTB-Stx2eB. The obtained neutralization epitope fragment and Sts2eB fragment were introduced into pYES2 LTB-Stx2eB via homologous recombination using GeneArt Seamless PLUS Cloning and Assembly Kits (Invitrogen), thereby adding the antigen region to the C-terminus thereof (FIG. 5).

As a porcine parvovirus neutralization epitope, a sequence (VEQHNPINAGTELSAT: SEQ ID NO: 39) derived from a capsid protein VP2 neutralization epitope was used (Kamstrup et al., Virus Research, 1998, 53, 163-173). This epitope has a sequence that is highly maintained among cell lines. The DNA sequence is represented, for example, by 5'-gtggagcagcacaaccccatcaacgccggcaccgagctgtccgccacc-3' (SEQ ID NO: 40).

DNA of the neutralization epitope region was prepared by conducting annealing of a PP-F primer (5'-TGGTTCTCCTAGATCC gtg gag cag cac aac ccc atc aac gcc ggc acc gag ctg-3':SEQ ID NO: 41) and a PP-R primer (5'-CCTAGAGCTCCCGGGTACTATCAGTCCTT ggt ggc gga cag ctc ggt gcc ggc gtt gat-3':SEQ ID NO: 42) and an elongation reaction by DNA polymerase. The obtained neutralization epitope fragment and the above mentioned Sts2eB fragment were introduced into pYES2 LTB-Stx2eB via homologous recombination using GeneArt Seamless PLUS Cloning and Assembly Kits (Invitrogen), thereby adding the antigen region to the C-terminus thereof.

As a feline immunodeficiency virus neutralization epitope, a sequence (GSWMRAISSWRHRNRWEWRPDF: SEQ ID NO: 43) derived from an envelope protein gp120 neutralization epitope was used (Lombardi et al., Journal of Virology, 1993, 67, 4742-4749). This epitope has a sequence that is highly maintained among cell lines. The DNA sequence is represented, for example, by 5'-ggctcctggatgagggccatctcctcctggaggcacaggaacaggtgggagtggaggccgactt-3' (SEQ ID NO: 44).

DNA of the neutralization epitope region was prepared by conducting annealing of an FIV-F primer (5'-TGGTTCTCCTAGATCC ggc tcc tgg atg agg gcc atc tcc tgg agg-3': SEQ ID NO: 45), an FIV-M primer (5'-ctc cca cct gtt cct gtg cct cca gga gga gat ggc-3': SEQ ID NO: 46), and an FIV-R primer (5'-CCITAGAGCTCCCGGGTACTATCAGTCCTT gas gtc ggg cct cca ctc cca cct gtt cct gtg-3':SEQ ID NO: 47) and an elongation reaction by DNA polymerase. The obtained neutralization epitope fragment and the above mentioned Sts2eB fragment were introduced into pYES2 LTB-Stx2eB via homologous recombination using GeneArt Seamless PLUS Cloning and Assembly Kits (Invitrogen), thereby adding the antigen region to the C-terminus thereof.

As a porcine epidemic diarrhea virus neutralization epitope, a sequence (YSNIGVCKSSRGPRLQPYE: SEQ ID NO: 50) prepared by fusing two types of sequences (YSNIGVCK: SEQ ID NO: 48 (Chen et al., Viruses, 2013, 5, 2601-2613) and RGPRLQPYE: SEQ ID NO: 49) derived from a spike protein neutralization epitope was used (Deu et al., Virus Research 2008, 132, 192-196). This epitope has a sequence that is highly maintained among cell lines. The DNA sequence is represented, for example, by 5'-tactccaacatcggcgtctgcaagtcctcggggcccccggttgcagccctacgag-3' (SEQ ID NO: 51).

DNA of the neutralization epitope region was prepared by conducting annealing of a PED-F primer (5'-TGGTTCTCCTAGATCC tac tcc aac atc ggc gtc tgc aag tee tcc egg ggc ccc cgg-3': SEQ ID NO: 52) and a PED-R primer (5'-CCTTAGAGCTCCCGGGTACTATCAGTCCTT CTC GTA GGG CTG CAA CCG GGG GCC CCG GGA GGA CTT-3': SEQ ID NO: 53) and an elongation reaction by DNA polymerase. The obtained neutralization epitope fragment and the above mentioned Sts2eB fragment were introduced into pYES2 LTB-Stx2eB via homologous recombination using a GeneArt Seamless PLUS Cloning and Assembly Kit (Invitrogen), thereby adding the antigen region to the C-terminus thereof.

As a porcine rotavirus type A vaccine antigen candidate, a sequence (TEASTQIGDTEWKNSTTNPATFE-EVAKNEKL: SEQ ID NO: 56) prepared by fusing two types of sequences (TEASTQIGDTEWKN: SEQ ID NO: 54 and TTNPATFEEVAKNEKL: SEQ ID NO: 55) derived from a VP7 protein epitope (Nishikawa et al., Virology, 1989, 171, 503-515) was used. For example, the DNA sequence is represented by 5'-accgaggcctccacccagatcggcgacaccgagtg-gaagaactccaccaccaacegccaccttcgaggaggtggcc aagaacga-gaagttg-3' (SEQ ID NO: 57).

DNA of this region was prepared by conducting annealing of a RoA7-F primer (5'-TGGTICTCCTAGATCC acc gag gcc tcc acc cag atc ggc gac acc gag tgg aag aac tcc ace acc aac ccc gcc-3':SEQ ID NO: 58), a RoA7-M primer (5'-ggc cac ctc ctc gaa ggt ggc ggg gtt ggt ggt gga-3':SEQ ID NO: 59), and a RoA7-R primer (5'-CCTTAGAGCTCCCGGG-TACTATCAGTCCTT CAA CTT CTC GTT CTT GGC CAC CTC CTC GAA GGT GGC-3':SEQ ID NO: 60) and an elongation reaction with DNA polymerase. The obtained neutralization epitope fragment and the above mentioned Sts2eB fragment were introduced into pYES2 LTB-Stx2eB via homologous recombination using GeneArt Seamless PLUS Cloning and Assembly Kits (Invitrogen), thereby adding the antigen region to the C-terminus thereof.

As a porcine rotavirus type C vaccine antigen candidate, a sequence (NAAIGSPGPGKADGLLNDNNYAQSS-PASTETYEVVSNDTQL: SEQ ID NO: 63) prepared by fusing two types of sequences (NAAIGSPGPGKADG-LLNDNNYAQ: SEQ ID NO: 61 and SPASTETYEV-VSNDTQL: SEQ ID NO: 62) derived from a VP7 protein epitope was used. The DNA sequence is represented, for example, by 5'-aacgccgccatcggcccccgcaaggcccggctgct-gaacgcaacaactacgcccagtcctccccc gcctccaccgagacctacgag-gtggtgtccaacgacacccagctg-3' (SEQ ID NO: 64).

DNA of the region was prepared by conducting annealing of a RoC7-F primer (5'-TGGTTCTCCTAGATCC aac gcc gcc atc ggc tcc ccc ggc ccc ggc aag gcc gac ggc ctg ctg aac gac aac-3': SEQ ID NO: 65), a RoC7-M primer (5'-cac cac ctc gta ggt ctc ggt gga ggc ggg gga gga ctg ggc gta gtt gtt gtc gtt cag cag gcc gtc-3': SEQ ID NO: 66), and a RoC7-R primer (5'-CCTTAGAGCTCCCGGGTACTATCAGTCCTT cag ctg ggt gtc gtt gga cac cac ctc gta ggt ctc ggt-3': SEQ ID NO: 67) and an elongation reaction by DNA polymerase. The obtained neutralization epitope fragment and the above mentioned Sts2eB fragment were introduced into pYES2 LTB-Stx2eB via homologous recombination using GeneArt Seamless PLUS Cloning and Assembly Kits (Invitrogen), thereby adding the antigen region to the C-terminus thereof.

<Yeast Transformation and Protein Expression>

Yeast (*Saccharomyces cerevisiae* INVSc1, Invitrogen) was transformed as described below. Yeast was cultured overnight with shaking in YPD medium (1% yeast extract, 2% peptone, 2% dextrose (D-glucose)) at 30° C. and 200 rpm. The cultured product was diluted such that OD600 was adjusted to from 0.2 to 0.4 in 10 mL of YPD. Then, shaking culture was conducted at 30° C. and 200 rpm until OD600 fell in a range of 0.6 to 1.0. Centrifugation was performed at 500×g at room temperature for five minutes to obtain a pellet of cells. The supernatant was discarded. The pellet was suspended in 10 mL of Solution I (S.c. EasyComp Transformation Kit, Invitrogen). Centrifugation was performed at 500×g at room temperature for five minutes to obtain a pellet of cells. The supernatant was discarded. The pellet was suspended in 1 mL of Solution II (S.c. EasyComp Transformation Kit, Invitrogen). The suspension was dispensed into 50-μL portions so as to obtain competent cells. The cells were stored in a freezer at −80° C. until use (provided that rapid freezing in liquid nitrogen was not conducted to avoid damage on cell walls).

The obtained competent cells were thawed to room temperature, and 1 μg of pYES plasmid was added, and then 500 μL of Solution III (room temperature) was added and vortexed. The solution was shaken at 30° C. for one hour (with vortexing every 15 minutes). YPD medium in an amount of 1 mL was added, followed by shaking culture at 30° C. for one hour. Centrifugation was performed at 3,000×g and room temperature to obtain a pellet of cells. The supernatant was discarded. The pellet was suspended in 100 μL of Solution III and plated on SC-Ura medium containing 2% glucose (6.7 g/L yeast nitrogen base, 0.1 g/L adenine, 0.1 g/L arginine, 0.1 g/L cysteine, 0.1 g/L leucine, 0.1 g/L lysine, 0.1 g/L threonine, 0.1 g/L tryptophan, 0.05 g/L aspartic acid, 0.05 g/L, histidine, 0.05 g/L isoleucine, 0.05 g/L methionine, 0.05 g/L phenylalanine, 0.05 g/L proline, 0.05 g/L serine, 0.05 g/L tyrosine, 0.05 g/L valine), followed by static culture at 30° C. for two to four days.

Protein expression in yeast was induced as described below. A single colony of transformed yeast was cultured overnight with shaking at 30° C. and 200 rpm using SC-Ura medium containing 2% raffinose. Yeast cells required to achieve OD600 of 0.4 in 10 mL of the medium were collected by centrifugation (at 1,500×g and room temperature for five minutes), suspended in 10 mL of SC-Ura containing 2% galactose for expression induction. The cells were cultured with shaking at 30° C. and 200 rpm. Sampling was conducted over time.

<Western Analysis>

The thus obtained yeast culture solution in an amount of 200 μL was mixed with the same amount of a sample buffer (EZ Apply, manufactured by ATTO). The resultant was then mixed and heated for five minutes in boiling water to carry out SDS treatment of the sample. The electrophoresis (SDS-PAGE) of proteins was carried out using an electrophoresis tank (Mini Protean Tetracell) and Mini Protean TGX-gel (BIO RAD). An electrophoresis buffer (EZ Run, manufactured by ATTO) was added, 5 μl of the SDS-treated sample was applied to a well, and the electrophoresis was carried out at a constant voltage of 200 V for 40 minutes.

After the electrophoresis, the blotting of the gel was carried out using a Trans-Blot Transfer Pack (BIO RAD) and Trans-Blot Turbo (BIO RAD).

The blotted membrane was immersed in a blocking solution (TBS-based, pH 7.2, Nakalai Tesque, Inc.), followed by shaking at room temperature for one hour, or left to stand at 4° C. for 16 hours. The membrane was then shaken in TBS-T (137 mM sodium chloride, 2.68 mM potassium chloride, 1% polyoxyethylene sorbitan monolaurate, 25 mM Tris-HCl, pH 7.4) at room temperature for five minutes, and the shaking was repeated for a total of three times to carry out washing. For vaccine protein detection, an anti-Stx2eB monoclonal antibody, which was diluted 2,000-fold with TBS-T, was used. The membrane was immersed in the diluted solution and shaken at room temperature for two hours, thereby conducting an antigen-antibody reaction. The shaking in TBS-T at room temperature for five minutes was repeated for a total of three times to carry out washing. As a secondary antibody, Anti-Rat IgG, AP-linked Antibody (Promega), which was diluted 2,000-fold with TBS-T, was used. The membrane was immersed in the diluted solution and shaken at room temperature for one hour, thereby conducting an antigen-antibody reaction. The shaking in TBS-T at room temperature for five minutes was repeated for a total of three times to carry out washing. To carry out a chromogenic reaction with alkaline phosphatase, the washed membrane was immersed in a chromogenic solution (0.1 M sodium chloride, 5 mM chlorinated magnesium, 0.33 mg/ml nitro blue tetrazolium, 0.33 mg/ml 5-bromo-4-chloro-3-indolyl-phosphoric acid, 0.1 M Tris-HCl, pH 9.5), followed by shaking at room temperature for seven minutes. The membrane was then washed with distilled water and dried at normal temperature.

<Results>

Figure 6:
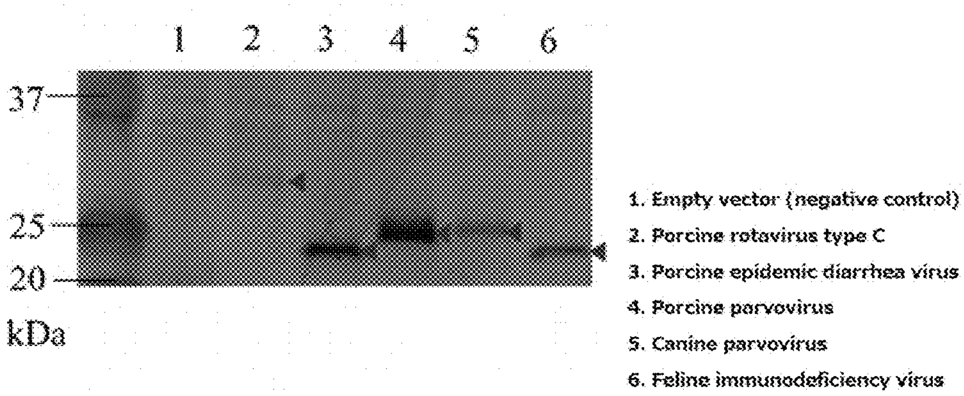
FIG. 6 is a photographic image showing the results of Western blot analysis of expression of the vaccine protein in yeast.

FIG. 6 illustrates the expression of each fusion antigen in gene recombinant yeast. The protein accumulation was confirmed for each vaccine.

Example 3

<Gene Construction>

A sequence (SDGAVQPDGGQPAVRNE: SEQ ID NO: 33) (hereinafter expressed as "VP2") derived from a capsid protein VP2 neutralization epitope serving as a canine parvovirus neutralization epitope was linked to the C-terminus of LTB-Stx2eB in the same manner as in Example 2. Further, 6×His to be used as a purification tag was fused therewith, thereby preparing a gene construct for causing the expression of the fusion protein added with the secretory signal peptide (LBVP2). The thus obtained gene construct was inserted into an *Escherichia coli* expression vector pET15b. The *Escherichia coli* BL21 pLys cell line was transformed with the resulting expression vector.

<Expression of Recombinant Proteins Using *Escherichia coli*>

Colonies of *Escherichia coli* having a recombinant plasmid were inoculated in four test tubes containing 5 mL of 2×YT medium containing 100 mg/L ampicillin and cultured overnight at 180 rpm and 37° C. This preculture solution in an amount of 20 ml was inoculated on 1 L of 2×YT medium containing 100 mg/L ampicillin and cultured at 180 rpm and 37° C. until O.D. 600 reached approximately 0.4. IPTG at a final concentration of 1 mM was added, followed by culture at 22° C. and 120 rpm for four hours. The culture solution was centrifuged at 8,000 rpm for five minutes. The thus obtained bacterial cells were stored at −80° C. until use.

<Preparation of Soluble Protein from *Escherichia Coli*>

A lysing solution (10 ml Bug buster, 90 ml Equi. Buffer, 500 ml DNaseI) in an amount of 100 ml was added to bacterial cells in an amount corresponding to 1 L of the culture solution such that the cells were lysed at room temperature for 30 minutes. Then, the cells were centrifuged at 8,000 rpm and 4° C. for 15 minutes. The supernatant was transferred to a new centrifuge tube and centrifugation was conducted two more times in the same manner. The obtained supernatant was used for purification.

<Purification by Affinity Column>

Figure 7:
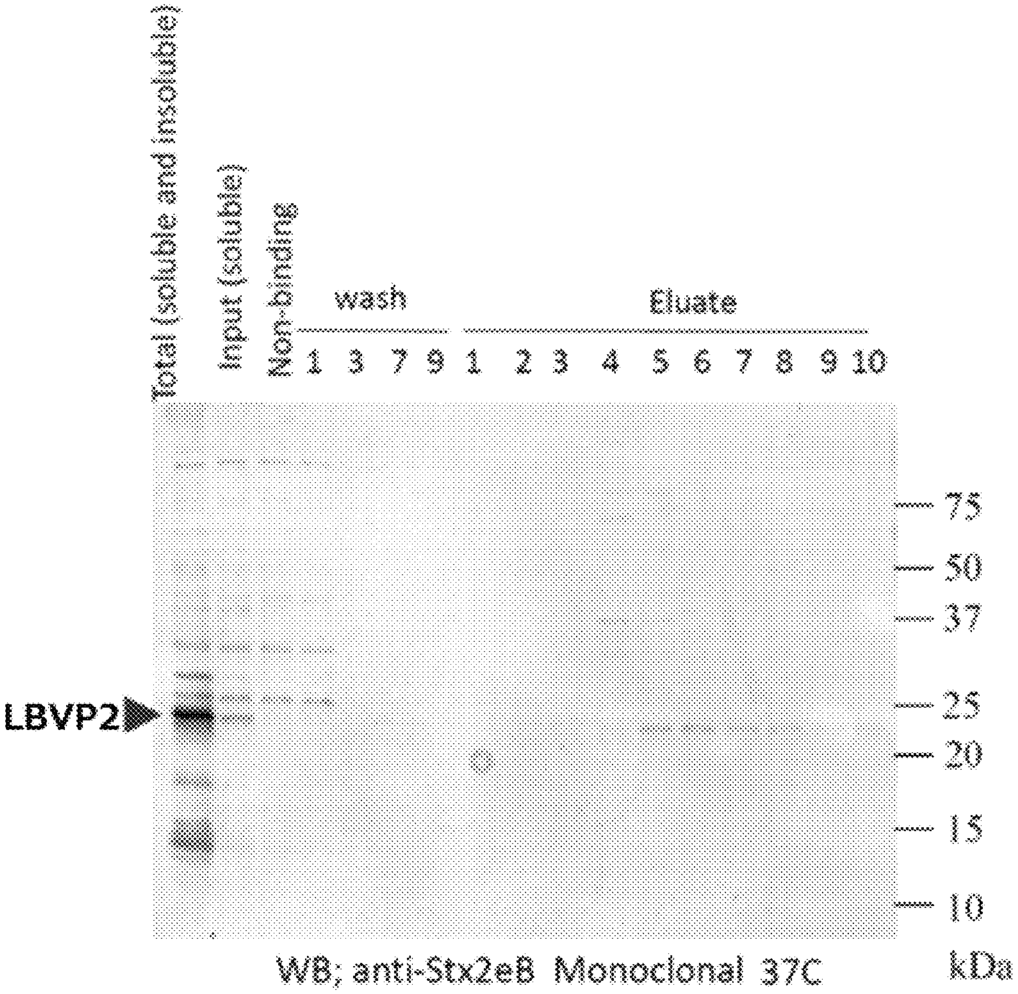
FIG. 7 is a photographic image of Western blot analysis results of purification of the vaccine protein (LBVP2) expressed in *Escherichia coli.*

Purification was conducted using TALON (Cobalt) (Clontech). An Econo-Pac column (BIO-RAD) was loaded with 5 ml of resin, and 50 ml of Equi. Buffer was allowed to pass therethrough for equilibrating. The above-mentioned protein solution was mixed with the resin at room temperature for 30 minutes. This suspension was returned back to the Econo-Pac column and the protein solution was allowed to pass therethrough. Equi. Buffer in an amount of 5 ml was allowed to pass therethrough ten times so as to wash non-binding proteins. After measurement at O.D. 280, it was confirmed that no protein was eluted. Elution Buffer in an amount of 2 ml was added. The eluate was collected into a 2 ml tube. This elution operation was repeated nine more times. Thus, 10 elution fractions were obtained. The resin was washed with Equi. Buffer. As illustrated in FIG. 7, purification of LBVP2 was confirmed.

<Immunization of Rabbits>

The purified antigen in an amount of 200 mg was injected with a complete adjuvant into foot pads of two rabbits. Four weeks later, the antigen in an amount of 100 mg was injected with a complete adjuvant into foot pads of two rabbits. Preliminary blood sampling was conducted before immunization. Interim blood sampling was conducted four or five weeks after the initial immunization. Exsanguination was conducted six weeks later.

<Measurement of Antibody Titer>

Figure 8:
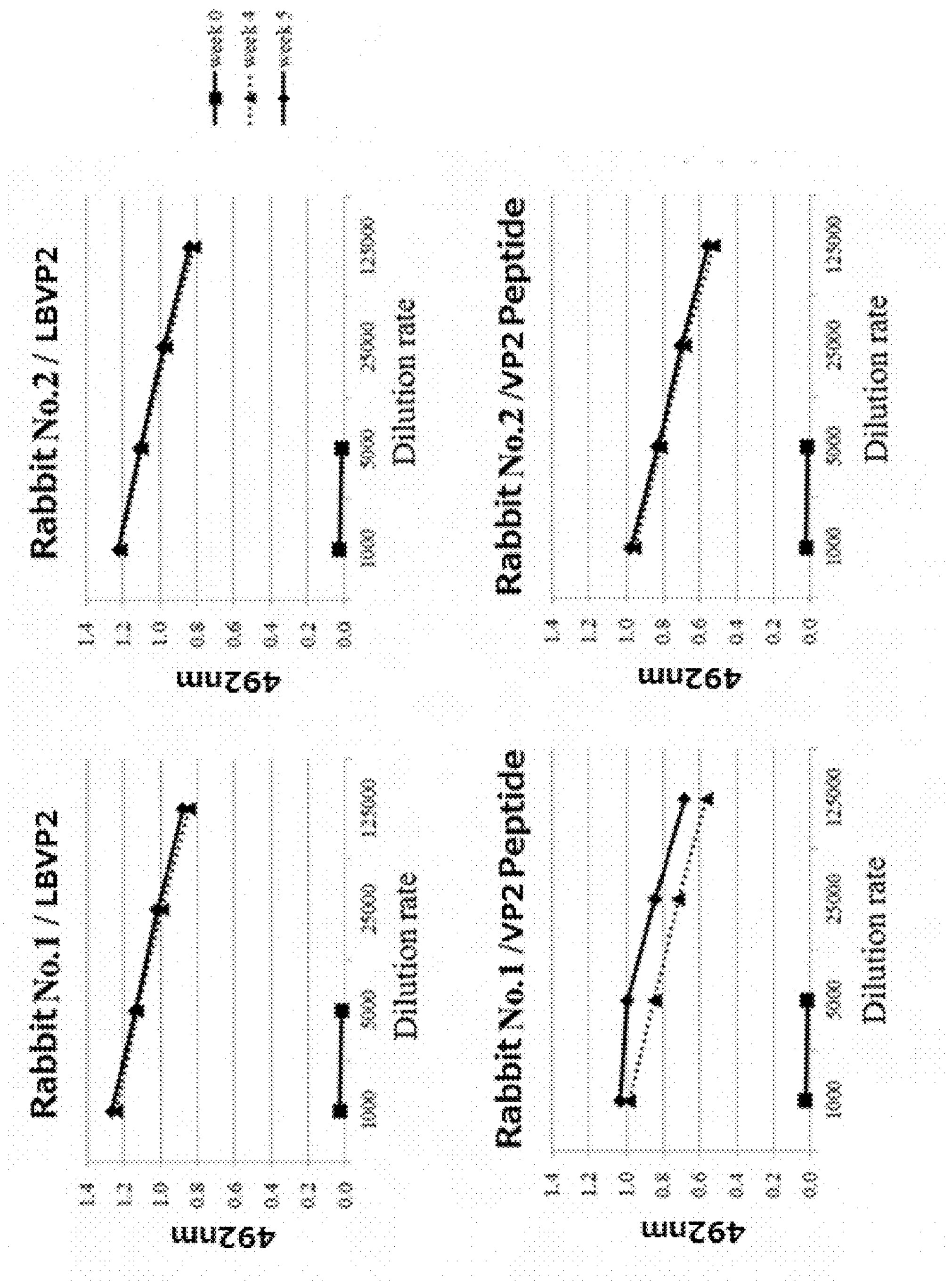
FIG. 8 shows the evaluation results of antibody titers (in relation to the dilution rate) in rabbits immunized with the vaccine protein (LBVP2) by solid phase ELISA of LBVP2 or VP2.
Figure 9:
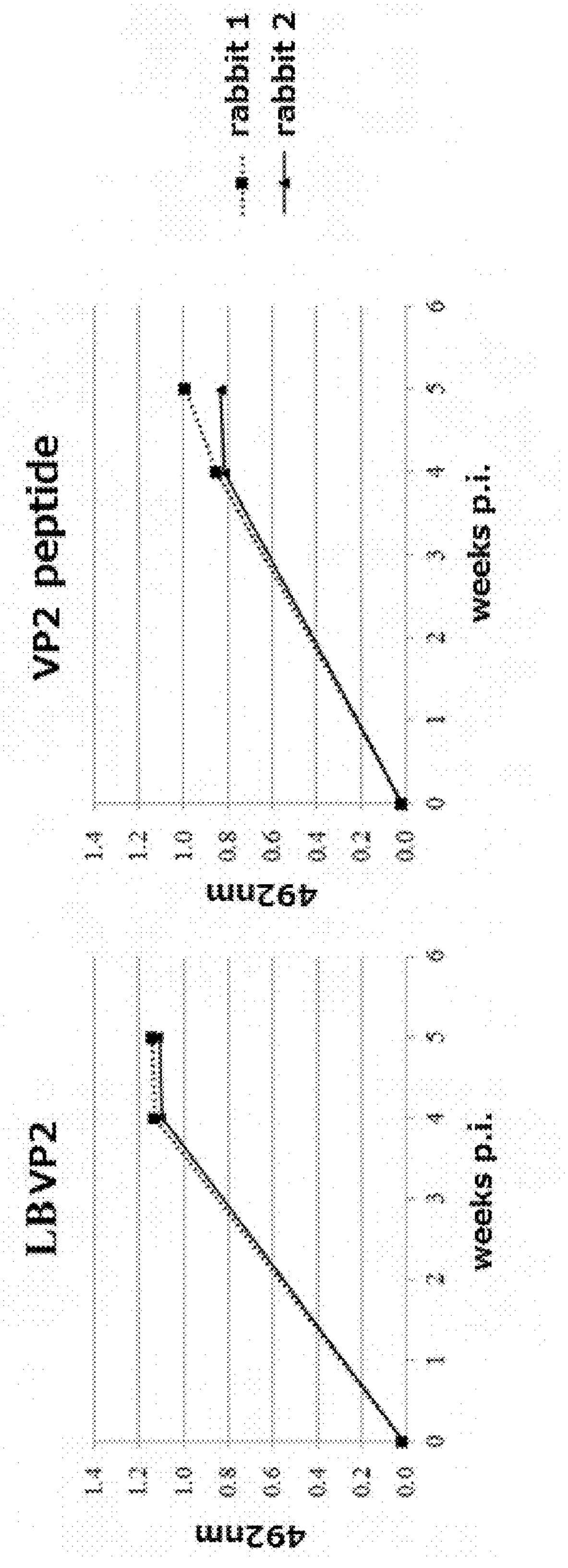
FIG. 9 shows the evaluation results of antibody titers (time-dependent changes) in rabbits immunized with the vaccine protein (LBVP2) by solid phase ELISA of LBVP2 or VP2, for which 5000-fold diluted blood was used.

Each obtained blood sample was 1000-fold, 5000-fold, 25000-fold, and 125000-fold diluted and then a solid phase of the immunizing antigen (LBVP2) or VP2 synthetic peptide (MSDGAVQPDGGQPAVRNERATG: SEQ ID NO: 68) was prepared, followed by performing ELISA. As a result, the titers of the antibodies against LBVP2 and the synthetic VP2 peptide were confirmed to have increased (FIGS. 8 and 9).

Example 4

<Production of Gene Recombinant Lettuce>

Figure 10:
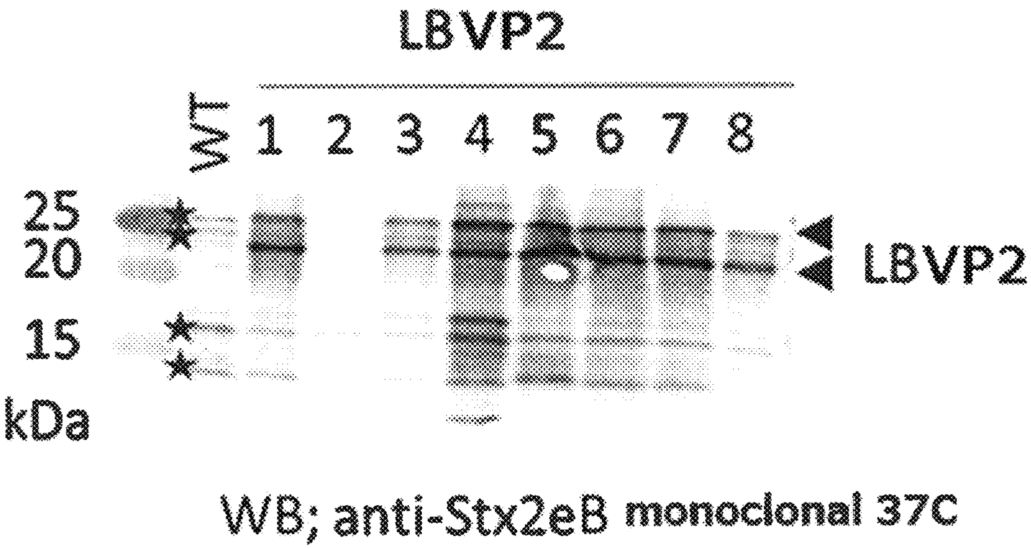
FIG. 10 is a photographic image of the expression of the LBVP2 vaccine protein in lettuce. Each triangle represents the LBVP2 protein. Each star symbol represents a nonspecific signal. The number on each lane represents a cell line number of an independent lettuce recombinant. WT represents a non-recombinant WT-derived sample.

The DNA fragment obtained by ligating a canine parvovirus neutralization epitope (hereinafter referred to as "VP2") to the C-terminus of LTB-Stx2eB described in Example 2 was inserted into pRI909, which is a plant expression vector described in Example 1. Gene recombinant lettuce was produced using the obtained plasmid in accordance with the method described in Example 1. Western analysis was conducted using the anti-Stx2eB antibody. As a result, the accumulation of the LBVP2 recombinant protein of interest was confirmed (FIG. 10). In addition, signals thought to be derived from glycosylation of LTB were also detected.

INDUSTRIAL APPLICABILITY

The fusion protein according to the present invention is useful in the field of livestock farming.

The invention claimed is:

1. A fusion protein, comprising:

an antigenic peptide, which is other than a glycoprotein 5-derived peptide of porcine reproductive and respiratory syndrome (PRRS) virus; and two or more proteins selected from the group consisting of a B subunit of Shiga toxin 2e (Stx2eB), a B subunit of *Escherichia coli* heat-labile toxin (LTB), and a B subunit of cholera toxin (CTB), wherein each of the antigenic peptide and the B subunits of the toxins that are components of said two or more proteins is linked in tandem via a peptide linker.

2. A fusion protein, comprising:

an antigenic peptide, which is other than a glycoprotein 5-derived peptide of porcine reproductive and respiratory syndrome (PRRS) virus; and an adjuvant protein, wherein the adjuvant protein comprises two or more proteins selected from the group consisting of a B subunit of Shiga toxin 2e (Stx2eB), a B subunit of *Escherichia coli* heat-labile toxin (LTB), and a B subunit of cholera toxin (CTB), wherein each of the antigenic peptide and the B subunits of the toxins that are components of said two or more proteins is linked in tandem via a peptide linker.

3. The fusion protein according to claim 1, wherein the antigenic peptide is a bacterial toxin-derived peptide.

4. The fusion protein according to claim 1, wherein the antigenic peptide is an *Escherichia coli* heat-stable enterotoxin (ST)-derived peptide.

5. The fusion protein according to claim 4, wherein the ST-derived peptide has an amino acid sequence having a sequence identity of 95% or more to the amino acid sequence of SEQ ID NO: 16.

6. The fusion protein according to claim 1, wherein the antigenic peptide is a mammalian infectious virus-derived peptide.

7. The fusion protein according to claim 6, wherein the mammalian infectious virus-derived peptide comprises a partial sequence of the parvovirus capsid protein VP2, feline immunodeficiency virus envelope protein gp120, porcine epidemic diarrhea virus spike protein, or rotavirus capsid protein VP7.

8. The fusion protein according to claim 7, wherein the partial sequence of the parvovirus capsid protein VP2 has an amino acid sequence having a sequence identity of 95% or more to the amino acid sequence of SEQ ID NO: 33 or 39, the partial sequence of the feline immunodeficiency virus envelope protein gp120 has an amino acid sequence having a sequence identity of 95% or more to the amino acid sequence of SEQ ID NO: 43, the partial sequence of the porcine epidemic diarrhea virus spike protein has an amino acid sequence having a sequence identity of 95% or more to the amino acid sequence of SEQ ID NO: 50, or the partial sequence of the rotavirus capsid protein VP7 has an amino acid sequence having a sequence identity of 80%1195% or more to the amino acid sequence of SEQ ID NO: 56 or 63.

9. The fusion protein according to claim 1, wherein the two or more proteins comprise Stx2eB and LTB.

10. The fusion protein according to claim 1, wherein the Asn residue at position 55 in the amino acid sequence of SEQ ID NO: 8 of Stx2eB is substituted by a Ser residue.

11. The fusion protein according to claim 1, wherein the peptide linker is PG12 (SEQ ID NO: 2), PG12v2 (SEQ ID NO: 4), PG17 (SEQ ID NO: 25), or PG22 (SEQ ID NO: 26) or a peptide having an amino acid sequence with a sequence identity of 95% or more to the sequence of any thereof.

12. The fusion protein according to claim 1, which has the amino acid sequence of SEQ ID NO: 20 or 22 or an amino acid sequence having a sequence identity of 95% or more to the amino acid sequence of SEQ ID NO: 20 or 22.

13. A DNA coding for the fusion protein according to claim 1.

14. A DNA construct comprising the DNA according to claim 13.

15. A recombinant vector comprising the DNA construct according to claim 14.

16. A transformant transformed with the recombinant vector according to claim 15.

17. The transformant according to claim 16, wherein the transformant is a plant or yeast.

18. A vaccine, comprising:

the fusion protein according to claim 1 or a transformant transformed with a recombinant vector comprising a DNA construct comprising a DNA coding for the fusion protein.

19. An animal feed, comprising:

the fusion protein according to claim 1 or a transformant transformed with a recombinant vector comprising a DNA construct comprising a DNA coding for the fusion protein.

20. A method for increasing immunity in a non-human mammal, comprising:

administering to a non-human mammal the fusion protein according to claim 1 or a transformant transformed with a recombinant vector comprising a DNA construct comprising a DNA coding for the fusion protein.

* * * * *